United States Patent
Raj et al.

(10) Patent No.: US 10,673,280 B2
(45) Date of Patent: Jun. 2, 2020

(54) SYSTEM, DEVICE, AND METHOD FOR COUPLED HUB AND SENSOR NODE ON-BODY ACQUISITION OF SENSOR INFORMATION

(71) Applicant: MC10, Inc., Lexington, MA (US)

(72) Inventors: Milan Raj, Natick, MA (US); Bryan McGrane, Cambridge, MA (US); Donald Fuchs, Wyckoff, NJ (US)

(73) Assignee: MC10, Inc., Lexington, MA (US)

( * ) Notice: Subject to any disclaimer, the term of this patent is extended or adjusted under 35 U.S.C. 154(b) by 0 days.

(21) Appl. No.: 15/437,967

(22) Filed: Feb. 21, 2017

(65) Prior Publication Data
US 2017/0244285 A1 Aug. 24, 2017

Related U.S. Application Data

(60) Provisional application No. 62/298,301, filed on Feb. 22, 2016.

(51) Int. Cl.
*H02J 50/12* (2016.01)
*H02J 7/02* (2016.01)
(Continued)

(52) U.S. Cl.
CPC ............ *H02J 50/12* (2016.02); *A61B 5/0024* (2013.01); *H02J 7/025* (2013.01); *H02J 50/20* (2016.02);
(Continued)

(58) Field of Classification Search
CPC ........ A61B 5/0024; H02J 50/12; H02J 50/80; H02J 7/025; H04B 5/0037; H04Q 2209/43; H04Q 2209/88; H04Q 9/00
(Continued)

(56) References Cited

U.S. PATENT DOCUMENTS 3,716,861 A 2/1973 Root
3,805,427 A 4/1974 Epstein
(Continued)

FOREIGN PATENT DOCUMENTS

CN 202068986 U 12/2011
DE 10 2006 011 596 A1 9/2007
(Continued)

OTHER PUBLICATIONS

U.S. Appl. No. 13/631,739, filed Sep. 28, 2012, C. Rafferty et al., Electronics for Detection of a Property of a Surface.
(Continued)

*Primary Examiner* — Ojiako K Nwugo
(74) *Attorney, Agent, or Firm* — Nixon Peabody LLP (57) ABSTRACT

An on-body sensor system includes a hub configured to be attached to a surface of a user. The hub being further configured to transmit electrical power and data signals into the surface and to receive response data signals from the surface. The system further including at least one sensor node configured to be attached to the surface or just below the skin. The system further including at least one sensor node being further configured to receive the electrical power and data signals from the hub through the surface and to transmit the response data signals into the surface. The electrical power from the hub powers the at least one sensor node and causes the at least one sensor node to generate sensor information that is transmitted back to the hub within the response data signals.

21 Claims, 5 Drawing Sheets

(51) Int. Cl.
*H02J 50/80* (2016.01)
*H04Q 9/00* (2006.01)
*H04B 5/00* (2006.01)
*A61B 5/00* (2006.01)
*H02J 50/20* (2016.01)

(52) U.S. Cl.
CPC ............ *H02J 50/80* (2016.02); *H04B 5/0037* (2013.01); *H04Q 9/00* (2013.01); *H04Q 2209/43* (2013.01); *H04Q 2209/88* (2013.01)

(58) Field of Classification Search
USPC ........................................ 340/870.31, 840.31
See application file for complete search history.

(56) References Cited

U.S. PATENT DOCUMENTS

| | | | |
|---|---|---|---|
| 3,838,240 A | 9/1974 | Schelhorn | |
| 4,278,474 A | 7/1981 | Blakeslee | |
| 4,304,235 A | 12/1981 | Kaufman | |
| 4,416,288 A | 11/1983 | Freeman | |
| 4,658,153 A | 4/1987 | Brosh | |
| 4,911,169 A | 3/1990 | Ferrari | |
| 5,059,424 A | 10/1991 | Cartmell | |
| 5,272,375 A | 12/1993 | Belopolsky | |
| 5,306,917 A | 4/1994 | Black | |
| 5,326,521 A | 7/1994 | East | |
| 5,331,966 A | 7/1994 | Bennett | |
| 5,360,987 A | 11/1994 | Shibib | |
| 5,471,982 A | 5/1995 | Edwards | |
| 5,454,270 A | 10/1995 | Brown | |
| 5,491,651 A | 2/1996 | Janic | |
| 5,567,975 A | 10/1996 | Walsh | |
| 5,580,794 A | 12/1996 | Allen | |
| 5,617,870 A | 4/1997 | Hastings | |
| 5,811,790 A | 9/1998 | Endo | |
| 5,817,008 A | 10/1998 | Rafert | |
| 5,907,477 A | 5/1999 | Tuttle | |
| 6,063,046 A | 5/2000 | Allum | |
| 6,220,916 B1 | 4/2001 | Bart | |
| 6,265,090 B1 | 7/2001 | Nishide | |
| 6,282,960 B1 | 9/2001 | Samuels | |
| 6,343,514 B1 | 2/2002 | Smith | |
| 6,387,052 B1 | 5/2002 | Quinn | |
| 6,410,971 B1 | 6/2002 | Otey | |
| 6,421,016 B1 | 7/2002 | Phillips | |
| 6,450,026 B1 | 9/2002 | Desarnaud | |
| 6,455,931 B1 | 9/2002 | Hamilton | |
| 6,567,158 B1 | 5/2003 | Falcial | |
| 6,626,940 B2 | 9/2003 | Crowley | |
| 6,628,987 B1 | 9/2003 | Hill | |
| 6,641,860 B1 | 11/2003 | Kaiserman | |
| 6,775,906 B1 | 8/2004 | Silverbrook | |
| 6,784,844 B1 | 8/2004 | Boakes | |
| 6,965,160 B2 | 11/2005 | Cobbley | |
| 6,987,314 B1 | 1/2006 | Yoshida | |
| 7,259,030 B2 | 8/2007 | Daniels | |
| 7,265,298 B2 | 9/2007 | Maghribi | |
| 7,302,751 B2 | 12/2007 | Hamburgen | |
| 7,337,012 B2 | 2/2008 | Maghribi | |
| 7,487,587 B2 | 2/2009 | Vanfleteren | |
| 7,491,892 B2 | 2/2009 | Wagner | |
| 7,521,292 B2 | 4/2009 | Rogers | |
| 7,557,367 B2 | 7/2009 | Rogers | |
| 7,618,260 B2 | 11/2009 | Daniel | |
| 7,622,367 B1 | 11/2009 | Nuzzo | |
| 7,727,228 B2 | 6/2010 | Abboud | |
| 7,739,791 B2 | 6/2010 | Brandenburg | |
| 7,759,167 B2 | 7/2010 | Vanfleteren | |
| 7,815,095 B2 | 10/2010 | Fujisawa | |
| 7,960,246 B2 | 6/2011 | Flamand | |
| 7,982,296 B2 | 7/2011 | Nuzzo | |
| 8,097,926 B2 | 1/2012 | De Graff | |
| 8,198,621 B2 | 6/2012 | Rogers | |
| 8,207,473 B2 | 6/2012 | Axisa | |
| 8,217,381 B2 | 7/2012 | Rogers | |
| 8,332,053 B1 | 12/2012 | Patterson | |
| 8,372,726 B2 | 2/2013 | De Graff | |
| 8,389,862 B2 | 3/2013 | Arora | |
| 8,431,828 B2 | 4/2013 | Vanfleteren | |
| 8,440,546 B2 | 5/2013 | Nuzzo | |
| 8,536,667 B2 | 9/2013 | De Graff | |
| 8,552,299 B2 | 10/2013 | Rogers | |
| 8,618,656 B2 | 12/2013 | Oh | |
| 8,664,699 B2 | 3/2014 | Nuzzo | |
| 8,679,888 B2 | 3/2014 | Rogers | |
| 8,729,524 B2 | 5/2014 | Rogers | |
| 8,754,396 B2 | 6/2014 | Rogers | |
| 8,865,489 B2 | 10/2014 | Rogers | |
| 8,886,334 B2 | 11/2014 | Ghaffari | |
| 8,905,772 B2 | 12/2014 | Rogers | |
| 9,012,784 B2 | 4/2015 | Arora | |
| 9,082,025 B2 | 7/2015 | Fastert | |
| 9,105,555 B2 | 8/2015 | Rogers | |
| 9,105,782 B2 | 8/2015 | Rogers | |
| 9,107,592 B2 | 8/2015 | Litt | |
| 9,119,533 B2 | 9/2015 | Ghaffari | |
| 9,123,614 B2 | 9/2015 | Graff | |
| 9,159,635 B2 | 10/2015 | Elolampi | |
| 9,168,094 B2 | 10/2015 | Lee | |
| 9,171,794 B2 | 10/2015 | Rafferty | |
| 9,186,060 B2 | 11/2015 | De Graff | |
| 9,226,402 B2 | 12/2015 | Hsu | |
| 9,247,637 B2 | 1/2016 | Hsu | |
| 9,289,132 B2 | 3/2016 | Ghaffari | |
| 9,295,842 B2 | 3/2016 | Ghaffari | |
| 9,320,907 B2 | 4/2016 | Bogie | |
| 9,324,733 B2 | 4/2016 | Rogers | |
| 9,372,123 B2 | 6/2016 | Li | |
| 9,408,305 B2 | 8/2016 | Hsu | |
| 9,420,953 B2 | 8/2016 | Litt | |
| 9,450,043 B2 | 9/2016 | Nuzzo | |
| 9,515,025 B2 | 12/2016 | Rogers | |
| 9,516,758 B2 | 12/2016 | Arora | |
| 9,545,216 B2 | 1/2017 | D'Angelo | |
| 9,545,285 B2 | 1/2017 | Ghaffari | |
| 9,554,850 B2 | 1/2017 | Lee | |
| 9,579,040 B2 | 2/2017 | Rafferty | |
| 9,583,428 B2 | 2/2017 | Rafferty | |
| D781,270 S | 3/2017 | Li | |
| 9,622,680 B2 | 4/2017 | Ghaffari | |
| 9,629,586 B2 | 4/2017 | Ghaffari | |
| 9,647,171 B2 | 5/2017 | Rogers | |
| 9,655,560 B2 | 5/2017 | Ghaffari | |
| 9,662,069 B2 | 5/2017 | De Graff | |
| 9,702,839 B2 | 7/2017 | Ghaffari | |
| 9,704,908 B2 | 7/2017 | De Graff | |
| 9,706,647 B2 | 7/2017 | Hsu | |
| 9,723,122 B2 | 8/2017 | Ghaffari | |
| 9,723,711 B2 | 8/2017 | Elolampi | |
| 9,750,421 B2 | 9/2017 | Ghaffari | |
| 9,757,050 B2 | 9/2017 | Ghaffari | |
| 9,905,105 B1 * | 2/2018 | Ikonen | G08B 21/0211 |
| 2001/0012918 A1 | 8/2001 | Swanson | |
| 2001/0021867 A1 | 9/2001 | Kordis | |
| 2002/0000813 A1 | 1/2002 | Hirono | |
| 2002/0026127 A1 | 2/2002 | Balbierz | |
| 2002/0079572 A1 | 6/2002 | Khan | |
| 2002/0082515 A1 | 6/2002 | Campbell | |
| 2002/0094701 A1 | 7/2002 | Biegelsen | |
| 2002/0107436 A1 | 8/2002 | Barton | |
| 2002/0113739 A1 | 8/2002 | Howard | |
| 2002/0128700 A1 | 9/2002 | Cross, Jr. | |
| 2002/0145467 A1 | 10/2002 | Minch | |
| 2002/0151934 A1 | 10/2002 | Levine | |
| 2002/0158330 A1 | 10/2002 | Moon | |
| 2002/0173730 A1 | 11/2002 | Pottgen | |
| 2002/0193724 A1 | 12/2002 | Stebbings | |
| 2003/0017848 A1 | 1/2003 | Engstrom | |
| 2003/0045025 A1 | 3/2003 | Coyle | |
| 2003/0097165 A1 | 5/2003 | Krulevitch | |
| 2003/0120271 A1 | 6/2003 | Burnside | |
| 2003/0162507 A1 | 8/2003 | Vatt | |
| 2003/0214408 A1 | 11/2003 | Grajales | |

(56) References Cited

U.S. PATENT DOCUMENTS

| | | |
|---|---|---|
| 2003/0236455 A1 | 12/2003 | Swanson |
| 2004/0006264 A1 | 1/2004 | Mojarradi |
| 2004/0085469 A1 | 5/2004 | Johnson |
| 2004/0092806 A1 | 5/2004 | Sagon |
| 2004/0106334 A1 | 6/2004 | Suzuki |
| 2004/0118831 A1 | 6/2004 | Martin |
| 2004/0135094 A1 | 7/2004 | Niigaki |
| 2004/0138558 A1 | 7/2004 | Dunki-Jacobs |
| 2004/0149921 A1 | 8/2004 | Smyk |
| 2004/0178466 A1 | 9/2004 | Merrill |
| 2004/0192082 A1 | 9/2004 | Wagner |
| 2004/0201134 A1 | 10/2004 | Kawai |
| 2004/0203486 A1 | 10/2004 | Shepherd |
| 2004/0221370 A1 | 11/2004 | Hannula |
| 2004/0238819 A1 | 12/2004 | Maghribi |
| 2004/0243204 A1 | 12/2004 | Maghribi |
| 2005/0021103 A1 | 1/2005 | DiLorenzo |
| 2005/0029680 A1 | 2/2005 | Jung |
| 2005/0067293 A1 | 3/2005 | Naito |
| 2005/0070778 A1 | 3/2005 | Lackey |
| 2005/0096513 A1 | 5/2005 | Ozguz |
| 2005/0113744 A1 | 5/2005 | Donoghue |
| 2005/0139683 A1 | 6/2005 | Yi |
| 2005/0171524 A1 | 8/2005 | Stern |
| 2005/0203366 A1 | 9/2005 | Donoghue |
| 2005/0204811 A1 | 9/2005 | Neff |
| 2005/0248312 A1 | 11/2005 | Cao |
| 2005/0261617 A1 | 11/2005 | Hall |
| 2005/0258050 A1 | 12/2005 | Bruce |
| 2005/0285262 A1 | 12/2005 | Knapp |
| 2006/0003709 A1 | 1/2006 | Wood |
| 2006/0011145 A1* | 1/2006 | Kates ............ A01K 15/02 119/719 |
| 2006/0038182 A1 | 2/2006 | Rogers |
| 2006/0071349 A1 | 4/2006 | Tokushige |
| 2006/0084394 A1 | 4/2006 | Engstrom |
| 2006/0106321 A1 | 5/2006 | Lewinsky |
| 2006/0122298 A1 | 6/2006 | Menon |
| 2006/0128346 A1 | 6/2006 | Yasui |
| 2006/0154398 A1 | 7/2006 | Qing |
| 2006/0160560 A1 | 7/2006 | Josenhans |
| 2006/0235314 A1 | 10/2006 | Migliuolo |
| 2006/0248946 A1 | 11/2006 | Howell |
| 2006/0257945 A1 | 11/2006 | Masters |
| 2006/0264767 A1 | 11/2006 | Shennib |
| 2006/0270135 A1 | 11/2006 | Chrysler |
| 2006/0276702 A1 | 12/2006 | McGinnis |
| 2006/0286785 A1 | 12/2006 | Rogers |
| 2007/0027514 A1 | 2/2007 | Gerber |
| 2007/0031283 A1 | 2/2007 | Davis |
| 2007/0108389 A1 | 5/2007 | Makela |
| 2007/0113399 A1 | 5/2007 | Kumar |
| 2007/0123756 A1 | 5/2007 | Kitajima |
| 2007/0139451 A1 | 6/2007 | Somasiri |
| 2007/0179373 A1 | 8/2007 | Pronovost |
| 2007/0190880 A1 | 8/2007 | Dubrow |
| 2007/0270672 A1 | 11/2007 | Hayter |
| 2007/0270674 A1 | 11/2007 | Kane |
| 2008/0036097 A1 | 2/2008 | Ito |
| 2008/0046080 A1 | 2/2008 | Vanden Bulcke |
| 2008/0074383 A1 | 3/2008 | Dean |
| 2008/0091089 A1 | 4/2008 | Guillory |
| 2008/0096620 A1 | 4/2008 | Lee |
| 2008/0139894 A1 | 6/2008 | Szydlo-Moore |
| 2008/0157235 A1 | 7/2008 | Rogers |
| 2008/0185534 A1 | 8/2008 | Simon |
| 2008/0188912 A1 | 8/2008 | Stone |
| 2008/0193749 A1 | 8/2008 | Thompson |
| 2008/0200973 A1 | 8/2008 | Mallozzi |
| 2008/0204021 A1 | 8/2008 | Leussler |
| 2008/0211087 A1 | 9/2008 | Mueller-Hipper |
| 2008/0237840 A1 | 10/2008 | Alcoe |
| 2008/0259576 A1 | 10/2008 | Johnson |
| 2008/0262381 A1 | 10/2008 | Kolen |
| 2008/0275327 A1 | 11/2008 | Faarbaek |
| 2008/0287167 A1 | 11/2008 | Caine |
| 2008/0297350 A1 | 12/2008 | Iwasa |
| 2008/0313552 A1 | 12/2008 | Buehler |
| 2009/0000377 A1 | 1/2009 | Shipps |
| 2009/0001550 A1 | 1/2009 | Li |
| 2009/0015560 A1 | 1/2009 | Robinson |
| 2009/0017884 A1 | 1/2009 | Rotschild |
| 2009/0048556 A1 | 2/2009 | Durand |
| 2009/0076363 A1 | 3/2009 | Bly |
| 2009/0088750 A1 | 4/2009 | Hushka |
| 2009/0107704 A1 | 4/2009 | Vanfleteren |
| 2009/0154736 A1 | 6/2009 | Lee |
| 2009/0184254 A1 | 7/2009 | Miura |
| 2009/0204168 A1 | 8/2009 | Kallmeyer |
| 2009/0215385 A1 | 8/2009 | Waters |
| 2009/0225751 A1 | 9/2009 | Koenck |
| 2009/0261828 A1 | 10/2009 | Nordmeyer-Massner |
| 2009/0273909 A1 | 11/2009 | Shin |
| 2009/0283891 A1 | 11/2009 | Dekker |
| 2009/0291508 A1 | 11/2009 | Babu |
| 2009/0294803 A1 | 12/2009 | Nuzzo |
| 2009/0317639 A1 | 12/2009 | Axisa |
| 2009/0322480 A1 | 12/2009 | Benedict |
| 2010/0002402 A1 | 1/2010 | Rogers |
| 2010/0030167 A1 | 2/2010 | Thirstrup |
| 2010/0036211 A1 | 2/2010 | La Rue |
| 2010/0059863 A1 | 3/2010 | Rogers |
| 2010/0072577 A1 | 3/2010 | Nuzzo |
| 2010/0073669 A1 | 3/2010 | Colvin |
| 2010/0087782 A1 | 4/2010 | Ghaffari |
| 2010/0090781 A1 | 4/2010 | Yamamoto |
| 2010/0090824 A1 | 4/2010 | Rowell |
| 2010/0116526 A1 | 5/2010 | Arora |
| 2010/0117660 A1 | 5/2010 | Douglas |
| 2010/0178722 A1 | 7/2010 | De Graff |
| 2010/0245011 A1 | 9/2010 | Chatzopoulos |
| 2010/0271191 A1 | 10/2010 | De Graff |
| 2010/0298895 A1 | 11/2010 | Ghaffari |
| 2010/0317132 A1 | 12/2010 | Rogers |
| 2010/0321161 A1 | 12/2010 | Isabell |
| 2010/0327387 A1 | 12/2010 | Kasai |
| 2011/0011179 A1 | 1/2011 | Gustafsson |
| 2011/0034760 A1 | 2/2011 | Brynelsen |
| 2011/0034912 A1 | 2/2011 | De Graff |
| 2011/0051384 A1 | 3/2011 | Kriechbaum |
| 2011/0054583 A1 | 3/2011 | Litt |
| 2011/0071603 A1 | 3/2011 | Moore |
| 2011/0098583 A1 | 4/2011 | Pandia |
| 2011/0101789 A1 | 5/2011 | Salter |
| 2011/0121822 A1 | 5/2011 | Parsche |
| 2011/0136436 A1 | 6/2011 | Hoyt |
| 2011/0140856 A1 | 6/2011 | Downie |
| 2011/0140897 A1 | 6/2011 | Purks |
| 2011/0148349 A1 | 6/2011 | Kim |
| 2011/0175735 A1 | 7/2011 | Forster |
| 2011/0184320 A1 | 7/2011 | Shipps |
| 2011/0185611 A1 | 8/2011 | Adams |
| 2011/0213559 A1 | 9/2011 | Pollack |
| 2011/0215931 A1 | 9/2011 | Callsen |
| 2011/0218756 A1 | 9/2011 | Callsen |
| 2011/0218757 A1 | 9/2011 | Callsen |
| 2011/0220890 A1 | 9/2011 | Nuzzo |
| 2011/0222375 A1 | 9/2011 | Tsubata |
| 2011/0263950 A1 | 10/2011 | Larson |
| 2011/0277813 A1 | 11/2011 | Rogers |
| 2011/0284268 A1 | 11/2011 | Palaniswamy |
| 2011/0306851 A1 | 12/2011 | Wang |
| 2011/0317737 A1 | 12/2011 | Klewer |
| 2012/0016258 A1 | 1/2012 | Webster |
| 2012/0051005 A1 | 3/2012 | Vanfleteren |
| 2012/0052268 A1 | 3/2012 | Axisa |
| 2012/0059235 A1 | 3/2012 | Davies |
| 2012/0065937 A1 | 3/2012 | De Graff |
| 2012/0074546 A1 | 3/2012 | Chong |
| 2012/0087216 A1 | 4/2012 | Keung |
| 2012/0091594 A1 | 4/2012 | Landesberger |
| 2012/0092178 A1 | 4/2012 | Callsen |
| 2012/0092222 A1 | 4/2012 | Kato |
| 2012/0101413 A1 | 4/2012 | Beetel |

(56) References Cited

U.S. PATENT DOCUMENTS

| | | |
|---|---|---|
| 2012/0101538 A1 | 4/2012 | Ballakur |
| 2012/0108012 A1 | 5/2012 | Yasuda |
| 2012/0126418 A1 | 5/2012 | Feng |
| 2012/0150072 A1 | 6/2012 | Revol-Cavalier |
| 2012/0150074 A1 | 6/2012 | Yanev |
| 2012/0157804 A1 | 6/2012 | Rogers |
| 2012/0165759 A1 | 6/2012 | Rogers |
| 2012/0172697 A1 | 7/2012 | Urman |
| 2012/0178367 A1 | 7/2012 | Matsumoto |
| 2012/0206097 A1 | 8/2012 | Scar |
| 2012/0215127 A1 | 8/2012 | Shikida |
| 2012/0220835 A1 | 8/2012 | Chung |
| 2012/0226130 A1 | 9/2012 | De Graff |
| 2012/0244848 A1 | 9/2012 | Ghaffari |
| 2012/0245444 A1 | 9/2012 | Otis |
| 2012/0256308 A1 | 10/2012 | Helin |
| 2012/0256492 A1 | 10/2012 | Song |
| 2012/0316455 A1 | 12/2012 | Rahman |
| 2012/0327608 A1 | 12/2012 | Rogers |
| 2013/0035751 A1 | 2/2013 | Shalev |
| 2013/0041235 A1 | 2/2013 | Rogers |
| 2013/0044215 A1 | 2/2013 | Rothkopf |
| 2013/0085552 A1 | 4/2013 | Mandel |
| 2013/0099358 A1 | 4/2013 | Elolampi |
| 2013/0100618 A1 | 4/2013 | Rogers |
| 2013/0116520 A1 | 5/2013 | Roham |
| 2013/0118255 A1 | 5/2013 | Callsen |
| 2013/0123587 A1 | 5/2013 | Sarrafzadeh |
| 2013/0150693 A1 | 6/2013 | D'Angelo |
| 2013/0185003 A1 | 7/2013 | Carbeck |
| 2013/0192356 A1 | 8/2013 | De Graff |
| 2013/0197319 A1 | 8/2013 | Monty |
| 2013/0200268 A1 | 8/2013 | Rafferty |
| 2013/0211761 A1 | 8/2013 | Brandsma |
| 2013/0214300 A1 | 8/2013 | Lerman |
| 2013/0215467 A1 | 8/2013 | Fein |
| 2013/0225965 A1 | 8/2013 | Ghaffari |
| 2013/0237150 A1 | 9/2013 | Royston |
| 2013/0245387 A1 | 9/2013 | Patel |
| 2013/0245388 A1 | 9/2013 | Rafferty |
| 2013/0253285 A1 | 9/2013 | Bly |
| 2013/0261415 A1 | 10/2013 | Ashe |
| 2013/0261464 A1 | 10/2013 | Singh |
| 2013/0274562 A1 | 10/2013 | Ghaffari |
| 2013/0285836 A1 | 10/2013 | Proud |
| 2013/0313713 A1 | 11/2013 | Arora |
| 2013/0316442 A1 | 11/2013 | Meurville |
| 2013/0316487 A1 | 11/2013 | De Graff |
| 2013/0316645 A1 | 11/2013 | Li |
| 2013/0320503 A1 | 12/2013 | Nuzzo |
| 2013/0321373 A1 | 12/2013 | Yoshizumi |
| 2013/0325357 A1 | 12/2013 | Walerow |
| 2013/0328219 A1 | 12/2013 | Chau |
| 2013/0331914 A1 | 12/2013 | Lee |
| 2014/0001058 A1 | 1/2014 | Ghaffari |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0097944 A1 | 4/2014 | Fastert |
| 2014/0110859 A1 | 4/2014 | Rafferty |
| 2014/0125458 A1 | 5/2014 | Bachman |
| 2014/0140020 A1 | 5/2014 | Rogers |
| 2014/0188426 A1 | 7/2014 | Fastert |
| 2014/0191236 A1 | 7/2014 | Nuzzo |
| 2014/0206976 A1 | 7/2014 | Thompson |
| 2014/0216524 A1 | 8/2014 | Rogers |
| 2014/0240932 A1 | 8/2014 | Hsu |
| 2014/0249520 A1 | 9/2014 | Ghaffari |
| 2014/0275835 A1 | 9/2014 | Lamego |
| 2014/0303452 A1 | 10/2014 | Ghaffari |
| 2014/0303680 A1 | 10/2014 | Donnelly |
| 2014/0308930 A1 | 10/2014 | Tran |
| 2014/0340857 A1 | 11/2014 | Hsu |
| 2014/0350883 A1 | 11/2014 | Carter |
| 2014/0371547 A1 | 12/2014 | Gartenberg |
| 2014/0374872 A1 | 12/2014 | Rogers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0025394 A1 | 1/2015 | Hong |
| 2015/0035680 A1 | 2/2015 | Li |
| 2015/0035743 A1 | 2/2015 | Rosener |
| 2015/0069617 A1 | 3/2015 | Arora |
| 2015/0099976 A1 | 4/2015 | Ghaffari |
| 2015/0100135 A1 | 4/2015 | Ives |
| 2015/0150505 A1 | 6/2015 | Kaskoun |
| 2015/0164377 A1 | 6/2015 | Nathan |
| 2015/0181700 A1 | 6/2015 | Rogers |
| 2015/0194817 A1 | 7/2015 | Lee |
| 2015/0237711 A1 | 8/2015 | Rogers |
| 2015/0241288 A1 | 8/2015 | Keen |
| 2015/0248833 A1 | 9/2015 | Arne |
| 2015/0260713 A1 | 9/2015 | Ghaffari |
| 2015/0272652 A1 | 10/2015 | Ghaffari |
| 2015/0286913 A1 | 10/2015 | Fastert |
| 2015/0320472 A1 | 11/2015 | Ghaffari |
| 2015/0335254 A1 | 11/2015 | Fastert |
| 2015/0342036 A1 | 11/2015 | Elolampi |
| 2016/0015962 A1 | 1/2016 | Shokoueinejad Maragheh |
| 2016/0027834 A1 | 1/2016 | de Graff |
| 2016/0045162 A1 | 2/2016 | De Graff |
| 2016/0049824 A1 | 2/2016 | Stein |
| 2016/0081192 A1 | 3/2016 | Hsu |
| 2016/0086909 A1 | 3/2016 | Garlock |
| 2016/0095652 A1 | 4/2016 | Lee |
| 2016/0099214 A1 | 4/2016 | Dalal |
| 2016/0099227 A1 | 4/2016 | Dalal |
| 2016/0111353 A1 | 4/2016 | Rafferty |
| 2016/0135740 A1 | 5/2016 | Ghaffari |
| 2016/0178251 A1 | 6/2016 | Johnson |
| 2016/0213262 A1 | 7/2016 | Ghaffari |
| 2016/0213424 A1 | 7/2016 | Ghaffari |
| 2016/0226298 A1* | 8/2016 | Shimokawa ............ H02J 7/025 |
| 2016/0228640 A1 | 8/2016 | Pindado |
| 2016/0232807 A1 | 8/2016 | Ghaffari |
| 2016/0240061 A1 | 8/2016 | Li |
| 2016/0249174 A1 | 8/2016 | Patel |
| 2016/0256070 A1 | 9/2016 | Murphy |
| 2016/0284544 A1 | 9/2016 | Nuzzo |
| 2016/0287177 A1 | 10/2016 | Huppert |
| 2016/0293794 A1 | 10/2016 | Nuzzo |
| 2016/0309594 A1 | 10/2016 | Hsu |
| 2016/0322283 A1 | 11/2016 | McMahon |
| 2016/0338646 A1 | 11/2016 | Lee |
| 2016/0361015 A1 | 12/2016 | Wang |
| 2016/0371957 A1 | 12/2016 | Ghaffari |
| 2016/0381789 A1 | 12/2016 | Rogers |
| 2017/0019988 A1 | 1/2017 | McGrane |
| 2017/0049397 A1 | 2/2017 | Sun |
| 2017/0071491 A1 | 3/2017 | Litt |
| 2017/0079588 A1 | 3/2017 | Ghaffari |
| 2017/0079589 A1 | 3/2017 | Ghaffari |
| 2017/0083312 A1 | 3/2017 | Pindado |
| 2017/0086747 A1 | 3/2017 | Ghaffari |
| 2017/0086748 A1 | 3/2017 | Ghaffari |
| 2017/0086749 A1 | 3/2017 | Ghaffari |
| 2017/0095670 A1 | 4/2017 | Ghaffari |
| 2017/0095732 A1 | 4/2017 | Ghaffari |
| 2017/0105795 A1 | 4/2017 | Lee |
| 2017/0110417 A1 | 4/2017 | Arora |
| 2017/0155427 A1* | 6/2017 | Hasan .................. H04B 5/0031 |
| 2017/0164865 A1 | 6/2017 | Rafferty |
| 2017/0186727 A1 | 6/2017 | Dalal |
| 2017/0188942 A1 | 7/2017 | Ghaffari |
| 2017/0200670 A1 | 7/2017 | Rafferty |
| 2017/0200707 A1 | 7/2017 | Rogers |
| 2017/0223846 A1 | 8/2017 | Elolampi |
| 2017/0244285 A1 | 8/2017 | Raj |

(56) References Cited

U.S. PATENT DOCUMENTS

2017/0244543 A1 8/2017 Raj
2017/0325684 A1* 11/2017 Vartiovaara .......... A61B 5/0017

FOREIGN PATENT DOCUMENTS

| | | |
|---|---|---|
| DE | 10 2007 046 886 A1 | 4/2009 |
| DE | 10 2008 044 902 A1 | 3/2010 |
| EP | 0585670 A2 | 3/1994 |
| EP | 0779059 A1 | 6/1997 |
| EP | 1808124 A2 | 7/2007 |
| EP | 2259062 A2 | 12/2010 |
| EP | 2498196 A2 | 9/2012 |
| EP | 2541995 A1 | 1/2013 |
| JP | 05-087511 A | 4/1993 |
| JP | 2005-052212 A | 3/2005 |
| JP | 2009-170173 A | 7/2009 |
| WO | WO 1999/038211 A2 | 7/1999 |
| WO | WO 2002/047162 A2 | 6/2002 |
| WO | WO 2003/021679 A2 | 3/2003 |
| WO | WO 2004/084720 A2 | 10/2004 |
| WO | WO 2005/083546 A1 | 9/2005 |
| WO | WO 2005/122285 A2 | 12/2005 |
| WO | WO 2007/003019 A2 | 1/2007 |
| WO | WO 2007/024983 A2 | 3/2007 |
| WO | WO 2007/116344 A1 | 10/2007 |
| WO | WO 2007/136726 A2 | 11/2007 |
| WO | WO 2008/030960 A2 | 3/2008 |
| WO | WO 2008/055212 A2 | 5/2008 |
| WO | WO 2009/036260 A1 | 3/2009 |
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/046883 A1 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/124898 A1 | 10/2011 |
| WO | WO 2011/127331 A2 | 10/2011 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/144738 A2 | 10/2013 |
| WO | WO 2013/144866 A1 | 10/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/124044 A1 | 8/2014 |
| WO | WO 2014/124049 A2 | 8/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |
| WO | WO 2015/077559 A1 | 5/2015 |
| WO | WO 2015/080991 A1 | 6/2015 |
| WO | WO 2015/102951 A2 | 7/2015 |
| WO | WO 2015/103483 A1 | 7/2015 |
| WO | WO 2015/103580 A2 | 7/2015 |
| WO | WO 2015/127458 A1 | 8/2015 |
| WO | WO 2015/134588 A1 | 9/2015 |
| WO | WO 2015/138712 A1 | 9/2015 |
| WO | WO 2015/145471 A1 | 10/2015 |
| WO | WO 2016/048888 A1 | 3/2016 |
| WO | WO 2016/054512 A1 | 4/2016 |
| WO | WO 2016/057318 A1 | 4/2016 |
| WO | WO 2016/081244 A1 | 5/2016 |
| WO | WO 2016/0127050 A1 | 8/2016 |
| WO | WO 2016/134306 A1 | 8/2016 |
| WO | WO 2016-140961 A1 | 9/2016 |
| WO | WO 2016/205385 A1 | 12/2016 |
| WO | WO 2017/015000 A1 | 1/2017 |
| WO | WO 2017/062508 A1 | 4/2017 |

OTHER PUBLICATIONS

U.S. Appl. No. 13/844,508, filed Mar. 15, 2013, S. Fastert et al., Monitoring Hit Count for Impact Events.
U.S. Appl. No. 14/294,808, filed Jun. 3, 2014, I. Kacyvenski et al., Motion Sensor and Analysis.
U.S. Appl. No. 14/311,686, filed Jun. 23, 2014, J. Fenuccio et al., Band With Conformable Electronics.
U.S. Appl. No. 14/510,868, filed Oct. 9, 2014, B. Ives, Utility Gear Including Conformal Sensors.
U.S. Appl. No. 14/524,817, filed Oct. 27, 2014, X. Li et al., Conformal Electronic Devices.
U.S. Appl. No. 14/588,765, filed Jan. 2, 2015, S. Lee et al., Integrated Devices for Low Power Quantitative Measurements.
U.S. Appl. No. 14/630,335, filed Feb. 24, 2015, B. Keen, Conformal Electronics with Deformation Indicators.
U.S. Appl. No. 14/656,046, filed Mar. 12, 2015, R. Ghaffari et al., Quantification of a Change in Assay.
U.S. Appl. No. 14/726,142, filed May 29, 2015, R. Ghaffari et al., Cardiac Catheter Employing Conformal Electronics for Mapping.
U.S. Appl. No. 14/746,659, filed Jun. 22, 2015, S. Fastert et al., Conformal Electronics Integrated With Apparel.
U.S. Appl. No. 14/758,946, filed Jul. 1, 2015, S. Fastert et al., Application for Monitoring a Property of a Surface.
U.S. Appl. No. 14/859,680, filed Sep. 21, 2015, D. Garlock, Methods and Apparatuses for Shaping and Looping Bonding Wires That Serve as Stretchale and Bendable Interconnects.
U.S. Appl. No. 14/870,719, filed Sep. 30, 2015, M. Dalal et al., Flexible Electronic Circuits With Embedded Integrated Circuit Die and Methods of Making and Using the Same.
U.S. Appl. No. 14/870,802, filed Sep. 30, 2015, M. Dalal et al., Flexible Interconnects for Modules of Integrated Circuits and Methods of Making and Using the Same.
U.S. Appl. No. 15/003,644, filed Jan. 21, 2016, Roozbeh Ghaffari et al., Methods of Detecting Parameters of a Lumen.
U.S. Appl. No. 15/016,937, filed Feb. 5, 2016, Jesus Pindado et al., Method and System for Interacting with an Environment.
U.S. Appl. No. 15/047,314, filed Feb. 18, 2016, Roozbeh Ghaffari et al., Catheter or Guidewire Device Including Flow Sensing and Use Thereof.
U.S. Appl. No. 15/048,576, filed Feb. 19, 2016, Shyamal Patel et al., Automated Detection and Confirguration of Wearable Devices Based on-Body Status, Location, and/or Orientation.
U.S. Appl. No. 15/057,762, filed Mar. 1, 2016, Brian Murphy et al., Perspiration Sensor.
U.S. Appl. No. 15/023,556, filed Mar. 21, 2016, Roozbeh Ghaffari, Conformal Sensor Systems for Sensing and Analysis.
U.S. Appl. No. 15/139,256, filed Apr. 26, 2016, Xia Li et al., Flexible Temperature Sensor Including Conformable Electronics.
U.S. Appl. No. 15/038,401, filed May 20, 2016, Huppert et al., Conformal Sensor Systems for Sensing and Analysis of Cardiac Activity.
U.S. Appl. No. 15/160,631, filed May 20, 2016, Lee et al., Ultra-Thin Wearable Sensing Device.
U.S. Appl. No. 15/183,513, filed Jun. 15, 2016, Wang et al., Moisture Wicking Adhesives for Skin Mounted Devices.

(56) References Cited

OTHER PUBLICATIONS

U.S. Appl. No. 15/189,461, filed Jun. 22, 2016, Ghaffari et al., Method and System for Structural Health Monitoring.
U.S. Appl. No. 15/194,995, filed Jun. 28, 2016, Hsu et al., Strain Isolation Structures for Stretchable Electronics.
U.S. Appl. No. 15/208,444, filed Jul. 12, 2016, McGrane et al., Conductive Stiffener, Method of Making a Conductive Stiffener, and Conductive Adhesive and Encapsulation Layers.
U.S. Appl. No. 15/238,488, filed Aug. 16, 2016, Sun et al., Wearable Heat Flux Devices and Methods of Use.
U.S. Appl. No. 15/119,559, filed Aug. 17, 2016, Elolampi et al., Multi-Part Flexible Encapsulation Housing for Electronic Devices.
U.S. Appl. No. 15/272,816, filed Sep. 22, 2016, Pindado et al., Method and System for Crowd-Sourced Algorithm Development.
U.S. Appl. No. 15/281,960, filed Sep. 30, 2016, Ghaffari et al., Method and System for Interacting with a Virtual Environment.
U.S. Appl. No. 15/286,129, filed Oct. 5, 2016, Ghaffari et al., Method and System for Neuromodulaton and Stimulation.
U.S. Appl. No. 15/337,389, filed Oct. 28, 2016, Arora et al, Extremely Stretchable Electronics.
U.S. Appl. No. 15/108,861, filed Jun. 29, 2016, McMahon et al, Encapsulated Conformal Electronic Systems and Devices, and Methods of Making and Using the Same.
U.S. Appl. No. 15/369,627, filed Dec. 5, 2016, Ghaffari et al., Cardiac Catheter Employing Conformal Electronics for Mapping.
U.S. Appl. No. 15/369,668, filed Dec. 5, 2016, Ghaffari et al., Cardiac Catheter Employing Conformal Electronics for Mapping.
U.S. Appl. No. 15/373,159, filed Dec. 8, 2016, Ghaffari et al., Catheter Balloon Methods and Apparatus Employing Sensing Elements.
U.S. Appl. No. 15/373,162, filed Dec. 8, 2016, Ghaffari et al., Catheter Balloon Methods and Apparatus Employing Sensing Elements.
U.S. Appl. No. 15/373,165, filed Dec. 8, 2016, Ghaffari et al., Catheter Balloon Methods and Apparatus Employing Sensing Elements.
U.S. Appl. No. 15/382,949, filed Dec. 19, 2016, Lee et al., Catheter Device Including Flow Sensing.
U.S. Appl. No. 15/405,166, filed Jan. 12, 2017, Rafferty et al., Electronics for Detection of a Condition of Tissue.
U.S. Appl. No. 15/413,218, filed Jan. 23, 2017, Rafferty et al., Electronics for Detection of a Condition of Tissue.
U.S. Appl. No. 15/412,993, filed Jan. 23, 2017, Rafferty et al., Embedding Thin Chips in Polymer.
U.S. Appl. No. 29/592,481, filed Jan. 31, 2017, Li et al., Electronic Device Having Antenna.
U.S. Appl. No. 15/433,873, filed Feb. 15, 2017, Rafferty et al., Electronics for Detection of a Condition of Tissue.
U.S. Appl. No. 15/437,964, filed Feb. 21, 2017, Raj et al., System, Devices, and Method for On-Body Data and Power Transmission.
U.S. Appl. No. 15/437,967, filed Feb. 21, 2017, Raj et al., System, Device, and Method for Coupled Hub and Sensor Node On-Body Acquisition of Sensor Information.
U.S. Appl. No. 15/457,852, filed Mar. 13, 2017, Dalal et al., Discrete Flexible Interconnects for Modules of Integrated Circuits.
U.S. Appl. No. 15/464,006, filed Mar. 20, 2017, Ghaffari et al., Systems, Methods, and Devices Using Stretchable or Flexible Electronics for Medical Applications.
U.S. Appl. No. 15/491,379, filed Apr. 19, 2017, Ghaffari et al., Method and System for Measuring Perspiration.
U.S. Appl. No. 15/498,941, filed Apr. 27, 2017, De Graff et al., Systems, Methods, and Devices Having Stretchable Integrated Circuitry for Sensing and Delivering Therapy.
U.S. Appl. No. 15/526,375, filed May 12, 2017, Aranyosi et al., Systems, Device, and Method for Electronic Device Activation.
U.S. Appl. No. 15/612,458, filed Jun. 2, 2017, Ghaffari et al., Integrated Devices to Facilitate Quantitative Assays and Diagnostics.
U.S. Appl. No. 15/614,469, filed Jun. 5, 2017, Hsu et al., Conformal Electronics Including Nested Serpentine Interconnects.
U.S. Appl. No. 15/620,181, filed Jun. 12, 2017, De Graff et al., Methods and Applications of Non-Planar Imaging Arrays.
U.S. Appl. No. 15/661,172, filed Jul. 27, 2017, Ghaffari et al., Catheter Balloon Employing Force Sensing Elements.
U.S. Appl. No. 12/968,637, filed Dec. 15, 2010, J. Rogers, High-Speed, High-Resolution Electrophysiology In-Vivo Using Conformal Electronics.
U.S. Appl. No. 13/492,636, filed Jun. 8, 2012, J. Rogers, Flexible and Stretchable Electronic Systems for Epidermal Electronics.
U.S. Appl. No. 14/155,010, filed Jan. 14, 2014, R. Nuzzo, Methods and Devices for Fabricating and Assembling Printable Semiconductor Elements.
U.S. Appl. No. 14/521,319, filed Oct. 22, 2014, J. Rogers, Stretchable and Foldable Electronic Devices.
U.S. Appl. No. 14/706,733, filed May 7, 2015, J. Rogers, Stretchable and Foldable Electronic Devices.
U.S. Appl. No. 15/084,211, filed Mar. 29, 2016, R. Nuzzo, Methods and Devices for Fabricating and Assembling Printable Semiconductor Elements.
U.S. Appl. No. 15/084,091, filed Mar. 29, 2016, R. Nuzzo, Methods and Devices for Fabricating and Assembling Printable Semiconductor Elements.
U.S. Appl. No. 15/084,122, filed Mar. 29, 2016, J. Rogers, Controlled Buckling Structures in Semiconductor Interconnects and Nanomembranes for Stretchable Electronics.
U.S. Appl. No. 15/217,121, filed Jul. 22, 2016, B. Litt, Flexible and Scalable Sensor Arrays for Recording and Modulating Physiologic Activity.
U.S. Appl. No. 15/339,338, filed Oct. 31, 2016, J. Rogers, A Stretchable Form of Single Crystal Silicon for High Performance Electronics on Rubber.
U.S. Appl. No. 15/470,780, filed Mar. 27, 2017, J. Rogers, Printed Assemblies of Ultrathin, Miscroscale Inorganic Light Emitting Diodes for Deformable and Semitransparent Displays.
U.S. Appl. No. 14/640,206, filed Jun. 30, 2017, R. Nuzzo, Methods and Devices for Fabricating and Assembliing Printable Semiconductor Elements.
Carvalhal et al., "Electrochemical Detection in a Paper-Based Separation Device", Analytical Chemistry, vol. 82, No. 3, (1162-1165) (4 pages) (Jan. 7, 2010).
Demura et al., "Immobilization of Glucose Oxidase with *Bombyx mori* Silk Fibroin by Only Stretching Treatment and its Application to Glucose Sensor," Biotechnology and Bioengineering, vol. 33, 598-603 (6 pages) (1989).
Ellerbee et al., "Quantifying Colorimetric Assays in Paper-Based Microfluidic Devices by Measuring the Transmission of Light through Paper," Analytical Chemistry, vol. 81, No. 20 8447-8452, (6 pages) (Oct. 15, 2009).
Halsted, "Ligature and Suture Material," Journal of the American Medical Association, vol. LX, No. 15, 1119-1126, (8 pages) (Apr. 12, 1913).
Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).
Kim et al., "Dissolvable Films of Silk Fibroin for Ultrathin Conformal Bio-Integrated Electronics," Nature, 1-8 (8 pages) (Apr. 18, 2010).
Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).
Kim et al., "Stretchable and Foldable Silicon Integrated Circuits," Science, vol. 320, 507-511 (5 pages) (Apr. 25, 2008).
Kim et al., "Electrowetting on Paper for Electronic Paper Display," ACS Applied Materials & Interfaces, vol. 2, No. 11, (3318-3323) (6 pages) (Nov. 24, 2010).
Ko et al., "A Hemispherical Electronic Eye Camera Based on Compressible Silicon Optoelectronics," Nature, vol. 454, 748-753 (6 pages) (Aug. 7, 2008).
Lawrence et al., "Bioactive Silk Protein Biomaterial Systems for Optical Devices," Biomacromolecules, vol. 9, 1214-1220 (7 pages) (Nov. 4, 2008).

(56) References Cited

OTHER PUBLICATIONS

Meitl et al., "Transfer Printing by Kinetic Control of Adhesion to an Elastomeric Stamp," Nature, vol. 5, 33-38 (6 pages) (Jan. 2006).
Omenetto et al., "A New Route for Silk," Nature Photonics, vol. 2, 641-643 (3 pages) (Nov. 2008).
Omenetto et al., "New Opportunities for an Ancient Material," Science, vol. 329, 528-531 (5 pages) (Jul. 30, 2010).
Siegel et al., "Foldable Printed Circuit Boards on Paper Substrates," Advanced Functional Materials, vol. 20, No. 1, 28-35, (8 pages) (Jan. 8, 2010).
Tsukada et al., "Structural Changes of Silk Fibroin Membranes Induced by Immersion in Methanol Aqueous Solutions," Journal of Polymer Science, vol. 32, 961-968 (8 pages) (1994).
Wang et al., "Controlled Release From Multilayer Silk Biomaterial Coatings to Modulate Vascular Cell Responses" Biomaterials, 29, 894-903 (10 pages) (Nov. 28, 2008).
Wikipedia, "Ball bonding" article [online]. Cited in PCT/US2015/051210 search report dated Mar. 1, 2016 with the following information "Jun. 15, 2011 [retrieved on Nov. 15, 2015}. Retrieved 12-18, 29 from the Internet: <URL: https://web.archive.org/web/20110615221003/hltp://en.wikipedia.org/wiki/Ball_Bonding>., entire document, especially para 1, 4, 5, 6," 2 pages, last page says ("last modified on May 11, 2011").
Bossuyt et al., "Stretchable Electronics Technology for Large Area Applications: Fabrication and Mechanical Characterizations", vol. 3, pp. 229-235 (7 pages) (Feb. 2013).
Jones et al., "Stretchable Interconnects for Elastic Electronic Surfaces". vol. 93, pp. 1459-1467 (9 pages) (Aug. 2005).
Lin et al., "Design and Fabrication of Large-Area, Redundant, Stretchable Interconnect Meshes Using Excimer Laser Photoablation and In Situ Masking", (10 pages) (Aug. 2010).
Kim et al., "A Biaxial Stretchable Interconnect With Liquid-Alloy-Covered Joints on Elastomeric Substrate", vol. 18, pp. 138-146 (9 pages) (Feb. 2009).
International Search Report and Written Opinion of International Searching Authority for Application No. PCT/US17/18672, dated May 10, 2017 (11 pages).
Extended European Search Report, European Application No. EP 17757056.1 (7 pages) (May 27, 2019).

\* cited by examiner

SYSTEM, DEVICE, AND METHOD FOR COUPLED HUB AND SENSOR NODE ON-BODY ACQUISITION OF SENSOR INFORMATION

CROSS-REFERENCE TO RELATED APPLICATIONS

The present application claims the benefit of and priority to U.S. Provisional Application No. 62/298,301, filed Feb. 22, 2016, and, "SYSTEM, DEVICE, AND METHOD FOR COUPLED HUB AND SENSOR NODE ON-BODY ACQUISITION OF SENSOR INFORMATION," which is hereby incorporated by reference herein in its entirety.

FIELD OF THE INVENTION

The present disclosure relates to on-body sensors. In particular, the present disclosure relates to acquiring sensor information from an on-body sensor by a hub.

BACKGROUND OF THE INVENTION

With advancements in the manufacturing of semiconductor devices, such devices are becoming smaller and more versatile. These devices are spurring advancements in different and new technological areas. One technological area is wearable devices. Within the technological area of wearable devices is the concept of location-specific sensors worn on a user to acquire sensor information. Despite the advancements in the semiconductor devices themselves, however, the current state of power sources still imposes limitations on the semiconductor devices. For example, the form factor and longevity of wearable devices are directly related to the on-board power sources. The power sources for wearable devices are typically in the form of bulky (relative to the size of the wearable devices), non-conformal batteries, such as lithium ion batteries, which present issues regarding, for example, placement of the sensor nodes on the body.

To counteract the issues presented by sensor nodes traditionally requiring on-board power supplies, advancements in wireless communications have allowed sensor nodes to instead be powered through wireless interrogation by a smart device (also referred to as a reader) that is brought into close proximity to the sensor node. However, such electrical power transmission requires the reader to be in constant proximity to the sensor node, which presents different issues than the sensor node having an on-board power source.

Further, there is a disparity between the rate of advancements related to sensor components on sensor nodes that allow for the acquisition of sensor information, and the rate of advancements in the backend components of sensor nodes used for processing, storing, and/or transmitting the sensor information off of the body.

Therefore, there is a continuing need for developing systems, methods, and devices that solve the above and related problems.

SUMMARY OF THE INVENTION

According to some embodiments, an interchangeable sensor system includes a hub configured to be attached to a user and to be selectively coupled to one or more sensor nodes. The hub is further configured to transmit electrical power and operational data wirelessly to the one or more sensor nodes. The system further includes at least one sensor node configured to be selectively coupled to the hub and to receive electrical power and transfer (e.g., send and receive) data wirelessly. The at least one sensor node includes at least one sensor configured to generate sensor data when electrical power is received from the hub. The at least one sensor node is further configured to transmit the sensor data wirelessly to the hub for processing, aggregation, and/or transmission to an off-body computer device. The at least one sensor node can also receive commands, instructions, firmware, algorithms, and system data updates wirelessly from the hub.

According to some additional embodiments, a method of acquiring sensor information is disclosed. The method includes, transmitting, by a hub, electrical power and optionally, operational data to at least one sensor node. The hub and at least one sensor node can be attached to a surface (e.g., the body of a user) and the at least one sensor node can be wirelessly, electrically, and/or physically coupled to the hub. The hub alternatively can be placed on the surface of the skin and the at least one sensor can be beneath the skin, just above the subcutaneous tissue. The method further includes the at least one sensor node receiving electrical power sufficient to power the sensor node and optionally, operational data, transmitted by the hub. The method further includes generating, by at least one sensor of the at least one senor node, sensor information associated with the body. The method further includes transmitting, by the at least one sensor node, the sensor information to the hub. The method further includes aggregating, processing, and/or analyzing, by the hub, the sensor information received from the at least one sensor node. The method is further described in that the electrical power, the operational data, or a combination thereof are transmitted to the at least one sensor node continuously, periodically, or semi-periodically by the hub for acquiring the sensor information associated with the body.

Additional aspects of the disclosure will be apparent to those of ordinary skill in the art in view of the detailed description of various embodiments, which is made with reference to the drawings, a brief description of which is provided below.

BRIEF DESCRIPTION OF THE DRAWINGS

The invention will be better understood from the following description of exemplary embodiments together with reference to the accompanying drawings, in which.

DETAILED DESCRIPTION OF THE ILLUSTRATED EMBODIMENTS

Although the present disclosure contains certain exemplary embodiments, it will be understood that the disclosure is not limited to those particular embodiments. On the contrary, the present disclosure is intended to cover all alternatives, modifications, and equivalent arrangements as may be included within the spirit and scope of the disclosure as further defined by the appended claims.

The present disclosure is directed to an interchangeable sensor system that includes a hub and one or more sensor nodes. The sensor nodes are configured to be coupled to the hub. By being coupled to the hub, the sensor nodes are converted from episodic sensor nodes to continuous sensor nodes. The sensor nodes and the hub are both configured to be coupled to a body of a user. The hub can be configured so that only one sensor node can be coupled to the hub, or multiple sensor nodes can be coupled to a hub, at any given time. In a coupled configuration, the hub wirelessly transmits electrical power and, optionally, data to the coupled sensor node. The wirelessly transmitted electrical power causes the sensor node to operate. Operation of the sensor node includes the sensor node acquiring (e.g., collecting and/or generating) sensor information based on signals received from one or more sensors within the sensor node. In some aspects, the wirelessly transmitted data further causes the sensor node to collect and/or generate sensor information, including location and/or sensor-specific information. Examples of sensor specific information include motion information (e.g., acceleration), temperature (e.g., ambient and of the sensor), electrical signals associated with cardiac activity, electrical signals associated with muscle activity, changes in electrical potential and impedance associated with changes to the skin, biopotential monitoring (e.g., electrocardiography (ECG), electromyography (EMG), and electroencephalogram (EEG)), bioimpedance monitoring (e.g., body-mass index, stress characterization, and sweat quantification), galvanic skin response information, optically modulated sensing (e.g., photoplethysmography and pulse-wave velocity). Upon collecting and/or generating the sensor information, the sensor node wirelessly transmits the sensor information back to the hub as, for example, response data that is responsive to the electrical power and data originally transmitted from the hub. The hub can be further configured to aggregate, process, and/or transmit the response data from the coupled sensor nodes to an off-body computer device, such as a smartphone, a tablet, a laptop, a desktop, etc., for further processing, aggregation, and/or transmission to additional computer devices, such as computer devices remote from the system.

The form factor of both the hub and the sensor nodes can allow for the coupled hub and senor nodes to be placed on an irregular surface, (e.g., the body of a user, such as on the surface of or under the skin of the user). When coupled to a surface of an object, the sensor node acquires sensor information pertaining to the object. When coupled to the surface of the body or an organ (e.g., the skin, the lungs, the heart, etc.), the sensor node acquires sensor information pertaining to the body and/or the organ. Moreover, the interchangeable nature of the sensor nodes with the hub allows for different types of sensor nodes to be coupled to the hub depending on the desired sensor information and/or location. Further, by removing the power source and the communications interface for the off-body computer device from the sensor node, updates to sensor nodes driven by developments in the sensors on the sensor nodes can be de-coupled from the more constant backend technology of the power source and the communications interface. Thus, sensor nodes can be replaced without having to replace, for example, the backend on-board power source and the communications interface of the hub and new sensor nodes can be developed for existing hubs. The separation of the sensor nodes from the hub facilitates focused designs that can take advantage of the disparate developments between sensors and backend system components. Advancements in sensors can be more quickly adapted and implemented into to the system. Further, advancements in backend components can similarly be more quickly adapted and implemented into the system.

Further, by coupling the sensor node to the hub, the paired sensor node and hub can provide continuous, periodic, and/or semi-periodic generation and/or collection of sensor information without requiring an off-body computer device in constant communication with the sensor node. Thus, the pairing of a sensor node with the hub provides for a more efficient and modular form factor for the acquisition of sensor information from an object, a subject, or a user, particularly in active situations, such as swimming, jogging, exercising, and the like, where an off-body computer device in constant communication with a sensor node is impractical or impossible.

Figure 1:
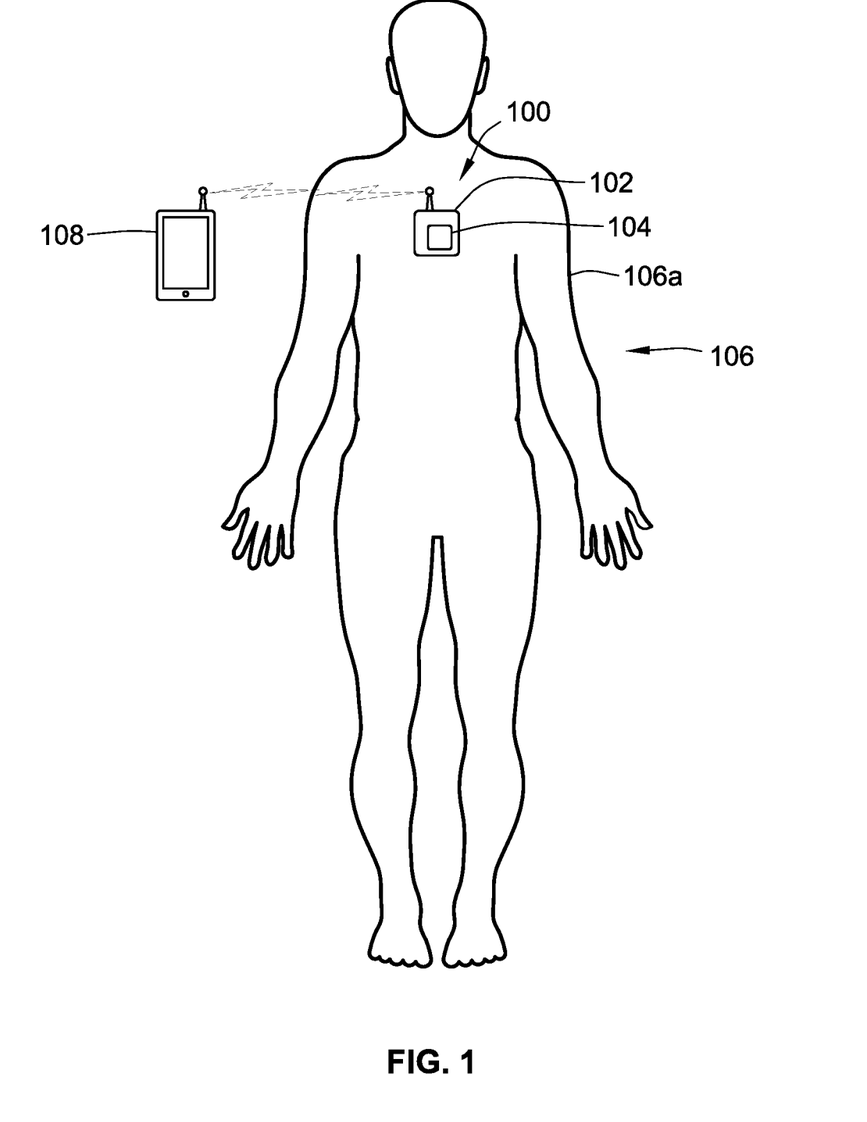
FIG. 1 shows a system including a sensor node coupled to a hub and attached to a user, in accord with aspects of the present disclosure.

Referring to FIG. 1, FIG. 1 shows a schematic view of a system 100, in accord with aspects of the present concepts. The system 100 includes two components, the hub 102 and the sensor node 104. As shown based on the overlap of the sensor node 104 on the hub 102, the sensor node 104 is configured to be coupled to the hub 102. Although only one hub 102 and one sensor node 104 are shown, the system 100 allows for multiple sensor nodes 104 that are interchangeably coupled to the hub 102. Further, although only one sensor node 104 is shown paired with the hub 102, in accordance with some embodiments of the invention, more than one sensor node 104 can be coupled to and paired with a single hub 102 at the same time.

The hub 102 and the sensor node 104, both when coupled and when un-coupled, are configured to attach to a surface, such as the skin of the body 106 of a user or the surface of an object. Specifically, the hub 102 and the sensor node 104 can be provided with an adhesive surface in order to attach the sensor node 104 to the surface 106a of the body 106 of the user. When attached to the surface 106a of the body 106, the sensor node 104 can collect and/or generate sensor information from the body 106.

As discussed above, the hub 102 provides for the backend components of the sensor node 104 within the system 100. The back end components can include, for example, the power source and the communications interface to provide for communication of data with an off-body computing device, such as a smart phone, laptop, or desktop computer (e.g., using Bluetooth, Bluetooth Low Energy, WiFi, Zigbee, medical telemetry or other wireless communication protocol). In relation to the sensor node 104, the hub 102 can provide electrical power for powering the sensor node 104 and data for providing algorithms and/or instructions for operation of the sensor node 104. Further, the hub 102 can include a processor, memory and computer programs for aggregating, processing, and/or storing sensor information received from the sensor node 104.

By providing both electrical power and optionally, data, to the sensor node 104, the hub 102 can selectively provide for continuous, periodic, and semi-periodic operation of the sensor node 104, in addition to on-demand operation of the sensor node 104, for the collection and/or generation of sensor information by the sensor node 104. Accordingly, the hub 102 replaces the need to manually interrogate the sensor node 104 with an off-body computer device, such as a smartphone, tablet, laptop, etc., that is repeatedly brought into range of the sensor node 104.

The hub 102 can have a generally standardized form factor, and provides a generally standardized platform for transferring electrical power and data to and from the sensor node 104. Accordingly, sensor nodes 104 can be designed around the standardized electrical power and data transfer protocols and requirements supported by the hub 102. The standardized design of the hub 102 accounts, in part, for the disparate development schedules between sensors and backend system components. Thus, the generally standardized electrical power and data transfer define design rules and constraints that allow for a sensor designer to design new and different sensor nodes that can be quickly and easily deployed and paired with the hub 102.

As shown in FIG. 1, the hub 102 can communicate with an off-body computer device 108. By way of example, and without limitation, upon aggregating, processing, and/or storing the sensor information, the hub 102 includes a communication interface 204 to communicate with the off-body computer device 108 and to transmit the sensor information to the off-body computer device 108. In accordance with some embodiments, the sensor information can include raw sensor data. Accordingly, the hub 102 handles the communications with the off-body computer device 108, which allows for the sensor nodes 104 to be simple and with fewer components that are only used for generating and/or collecting sensor information.

The sensor node 104 can be designed to target a specific sensing modality or a limited number of modalities (e.g., less than 5) that are related to specific locations on the body 106 of the user. The specific sensing modalities of the sensor node 104 can include, for example, heat flux, acceleration and angular velocity, or motion in general, electrical signals, such as electrocardiogram (ECG or EKG) and/or galvanic skin response signals, pressure, sweat, and blood oxygen saturation levels. However, the sensing modalities can include additional modalities not explicitly disclosed herein without departing from the spirit and scope of the present disclosure.

In some aspects, the sensor node 104 can be a simple sensor node in that all data for operation (e.g., initialization data, instructions, programs, and algorithms) is transmitted to the sensor node 104 from the hub 102. Thus, the sensor node 104 needs the electrical power and the data from the hub 102 to operate. Alternatively, the sensor node 104 may be a smart sensor node in that most, if not all, of the data required for operation is already stored on the sensor node 104. Thus, the sensor node 104 needs the electrical power and, optionally, triggering data only, for operation. In some aspects, the sensor node 104 may fall between the simple sensor node and the smart sensor node described above. For example, the sensor node 104 may have some data for operation already stored on the sensor node 104, but additional data for operation (e.g., for optional or advanced operation) can be transferred to the sensor node 104 from the hub 102.

In some aspects, the hub 102 transmits an "initiate" command via Near-Field Communication (NFC) to a sensor node 104, allowing the latter to execute a predetermined set of operations stored on a processor or stored on external memory on the sensor node 104. The sensor node 104 then performs sensing and collects and/or processes the sensor information in real time. The sensor node 104 then transmits the collected and/or processed data back to the hub 102 via NFC.

In some aspects, the hub 102 transmits a set of commands via NFC to the sensor node 104. The sensor node 104 then interprets and executes the set of commands in real time, such as by an on-board processor executing the commands. The sensor node 104 then performs sensing and transmits the sensory data back to the hub 102 via NFC. According to this aspect, the sensor node 104 can receive a command to enable sensing and a command to transmit the raw (e.g., not processed) senor information back to the hub 102 via NFC.

Figure 2:
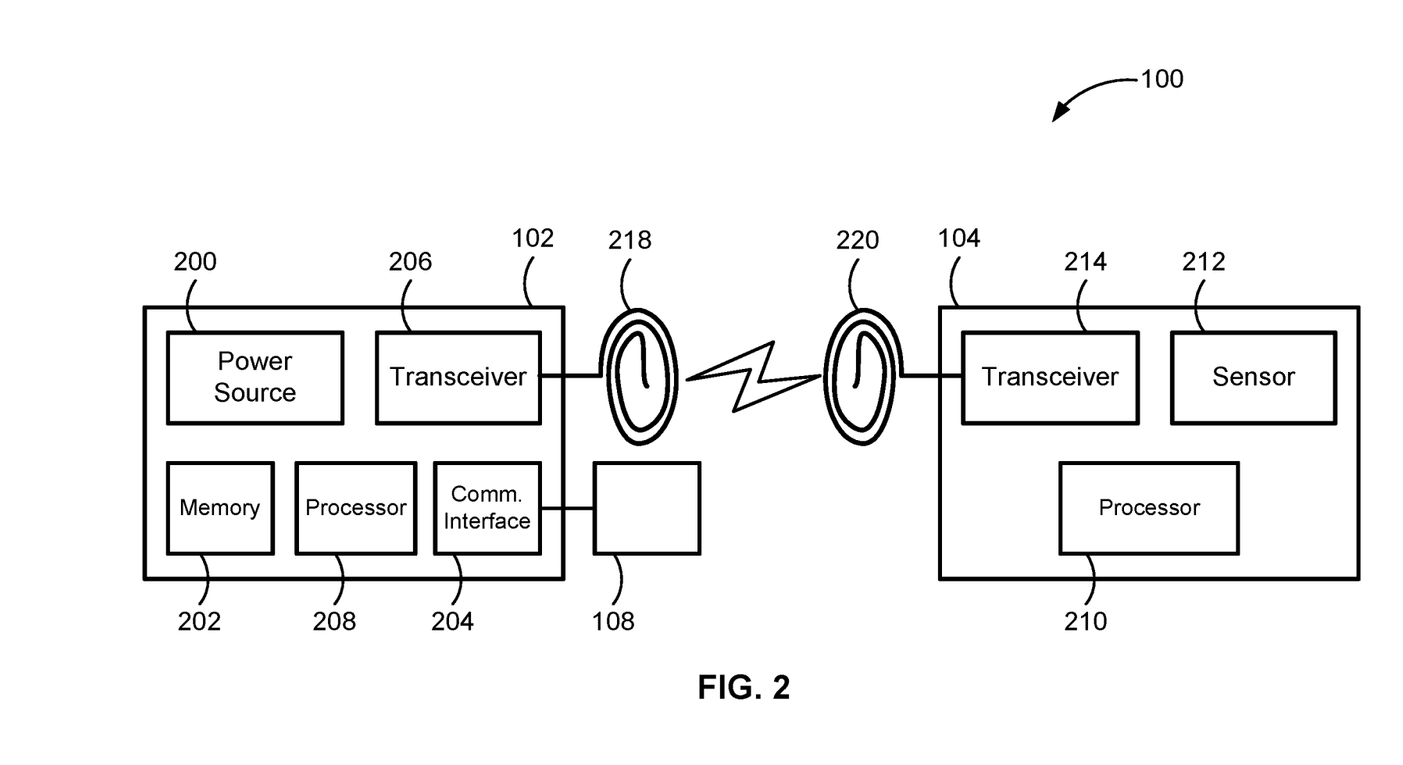
FIG. 2 shows a block diagram of the system of FIG. 1, in accord with aspects of the present disclosure.

Referring to FIG. 2, FIG. 2 shows a block diagram of the system 100 of FIG. 1, in accord with aspects of the present disclosure. Referring in detail first to the hub 102, the hub 102 includes, for example, a power source 200, memory 202, a communications interface 204 for communicating with the off-body computer device 108, a power transmitter and data transceiver 206 for communicating with the sensor node 104, and a processor 208.

The power source 200 provides the electrical power within the hub 102 and to the sensor node 104 within the system 100. The power source 200 can be various conventional power sources, such as a super-capacitor or one or more rechargeable or non-rechargeable batteries or cells having various battery chemistries, such as lithium ion (Li-ion), nickel-cadmium (NiCd), nickel-zinc (NiZn), nickel-metal hydride (NiMH), zinc and manganese(IV) oxide ($Zn/MnO_2$) chemistries, to name a few examples. In some aspects, the power source 200 can be an electrical wall outlet that the hub 102 directly connects to, or connects to through, for example, a power adapter (e.g., alternating current adapter). In some aspects, the power source 200 can be a component that harvests non-electrical energy, such as thermal energy, kinematic energy, and/or radio-frequency energy, and converts the energy into electrical energy. However, the power source 200 can be various other power sources not specifically disclosed herein.

The memory 202 stores various instructions and algorithms for both the functioning of the hub 102 and the sensor node 104. The memory 202 can be any type of conventional memory, such as read only memory (ROM), read-write memory (RWM), static and/or dynamic RAM, flash memory, and the like. In some aspects, data received from the off-body computer device 108 can be written to the memory 202 for updating the instructions and algorithms stored on the hub 102. For example, updated instructions and algorithms can be written to the memory to account for newly developed sensor nodes 104. Thus, rather than replacing the entire backend components, new instructions can be written to the hub 102 as new sensor nodes 104 are developed that require new data from the hub 102.

The communications interface 204 can be any traditional communications interface for communicating with the off-body computer device 108, such as one based on the wireless communication protocols of Wi-Fi, Bluetooth, Bluetooth Low Energy, Zigbee, and the like, based on 2.4 gigahertz (GHz) or 5 GHz radiofrequencies, and the like. However, the communications interface 204 can also support wired communications, such as wired communications with the off-body computer device 108, or with older sensor nodes 104 that do not support wirelessly receiving electrical power and data. Accordingly, in some aspects, the hub 102 can be backwards compatible with older sensor nodes that require wired connections.

In some aspects, the hub 102 is configured to communicate with only a particular type or kind of off-body computer device 108. For example, separate hubs 102 can be designed to be compatible with separate smartphones and/or tablets, and different hubs 102 can be used for communicating with different smartphones, such as smartphones running iOS®, ANDROID™, and the like. Thus, in some aspects, although each hub 102 is compatible with all of the sensor nodes 104 within the system 100, certain hubs 102 may be compatible only with certain off-body computer devices 108. A user can select the hub 102 that is compatible with the particular off-body computer device 108 that the user wants to use with the system 100.

The power transmitter and data transceiver 206 is configured to transmit electrical power and data to the sensor nodes 104. In some aspects, the power transmitter and data transceiver 206 is configured to modulate the electrical power with the data (e.g., analog data signals) to transmit the data on the carrier of the electrical power. Thus, electrical power and data can then be received by the sensor node 104 and demodulated and/or rectified to cause the sensor node 104 to operate. In some aspects, the transceiver 206 includes an NFC reader integrated circuit for interrogating the sensor node 104 based on the NFC protocol. In such a configuration, the hub 102 further includes a conductive coil 218. The transceiver 206 or, more particularly the coil 218, is located on the hub 102 so that the coil 218 is co-located with the corresponding transceiver or coil of the sensor node 104, as discussed further below. The co-location of the coil 218 with the sensor node 104 promotes more efficient transmission of the electrical power and data between the hub 102 and the sensor node 104. Although the NFC wireless protocol is predominately discussed herein, other wireless power protocols can be used including, for example, Qi (available from the Wireless Power Consortium, Piscataway, N.J.) or inductive, resonant and uncoupled (long distance) power transfer technologies (available from the AirFuel Alliance, Beaverton, Oreg.).

The processor 208 controls the operation of the hub 102. The processor 208 can be various types of processors, including microprocessors, microcontrollers (MCUs), etc., that are capable of executing algorithms and data processing. Specifically, the processor 208 executes one or more instructions and/or algorithms stored in the memory 202 or transmitted from the off-body computer device 108, which causes the hub 102 to transmit electrical power and data to the sensor nodes 104, receive response data from the sensor nodes 104, and aggregate, process, analyze, and/or store the response data. In some aspects, the processor 208 analyzes and/or processes the response data from the sensor nodes 104, such as the sensor information, prior to transmitting the response data to the off-body computer device 108. In addition, or in the alternative, the processor 208 can simply cause the hub 102 to transmit the response data to the off-body computer device 108, such as when the off-body computer device 108 is actively communicating with the hub 102.

Referring to the sensor node 104, the sensor node 104 is a location specific sensory platform that is placed at specific locations on the body for location-specific sensing. The sensor node 104 receives the transmitted electrical power and data from the hub 102 to perform sensing and communicate back to the hub 102. Further, because the sensor node 104 receives the electrical power from the hub 102 required for operation, the sensor node 104 does not include on-board power storage for the overall operation of the sensor nodes 104 (e.g., excluding power sources, such as capacitors, for temporary power disruption or small power sources, such as small batteries for temporary power). By not including an on-board power source, the form factor of the sensor node 104 can be reduced, among other benefits.

In some aspects, the sensor node 104 may merely stream sensor information back to the hub 102. Such a sensor node 104 may be considered a simple node. Alternatively, the sensor node 104 may store the sensor information on the sensor node 104 prior to transmitting the sensor information to the hub 102. Still further, the sensor node 104 may alternatively process the sensor information prior to transmitting the sensor information to the hub 102. Processing of the sensor information may include, for example, smoothing the data, analyzing the data, compressing the data, filtering the data, and the like. Such a sensor node 104 may be considered a smart node. Thus, the functionality of the sensor node 104 may vary.

The configuration of the sensor node 104 can vary depending on the specific modality and/or functionality of the sensor(s). However, in general, the sensor node 104 includes a processor 210, one or more sensors 212, and an electrical power receiver and data transceiver 214.

The processor 210 can be various types of processors, including microprocessors, MCUs, etc., that are capable of executing algorithms and data processing, particularly based on the low electrical power transmitted from the hub 102. In some aspects, the processor 210 can include memory for storing one or more algorithms performed by the sensor node 104 and/or the processor 210, and for storing information transmitted from the hub 102. Alternatively, or in addition, the sensor node 104 may include memory that is independent from the processor 210.

As discussed above, in some embodiments, the sensor node 104 is a simple node and functions based only on the data communicated from the hub 102. In such a case, the sensor node 104 does not include on-board instructions, algorithms, or other data required for functioning. Alternatively, the sensor node 104 can be a smart node that receives electrical power and triggering instructions (e.g., data) from the hub 102, but otherwise includes the necessary instructions, algorithms, or data internally for generating and/or collecting sensor information.

In the case of a simple sensor node 104, the hub 102 acts as the backend intelligence and power supply for the sensor node 104. Moreover, even in the case of a smart sensor node 104, the hub 102 can provide additional intelligence in the form of more advanced data processing. By way of example, and without limitation, the processor 210 can be a Cortex-M Series MCU by ARM® Ltd., an MSP430 MCU by Texas Instruments Inc., and the like.

The one or more sensors 212 perform the sensing functionality on the sensor node 104. The sensors 212 can be various types of sensors having various types of sensing modalities. According to some embodiments, the sensors 212 include heat flux sensors, accelerometers or gyroscopes (e.g., motions sensors), electrocardiogram (ECG or EKG) sensors, pressure sensors, heart rate monitors, galvanic skin response sensors, sweat sensors, non-invasive blood pressure and blood oxygen saturation monitors, pedometers, optical sensors, acoustic sensors, blood glucose sensors, and the like. However, the sensor node 104 can include additional sensors not explicitly disclosed herein without departing from the spirit and scope of the present disclosure. By way of some specific examples, the one or more sensors 212 can include an ADS1191 biopotential sensor by Texas Instruments, Inc., an ADXL362 accelerometer by Analog Devices, and the like.

The power receiver and data transceiver 214 allows the sensor node 104 to receive electrical power from the hub 102, and receive and transmit data communication from and to the hub 102. The transceiver 214 extracts the data from the electrical power to both power the sensor node 104 and provide the data for executing algorithms and processing data generated by the sensors 212. In some aspects, the transceiver 214 includes an NFC tag integrated circuit, such as an NFC energy harvester circuit, for responding to interrogation from the sensor node 104 based on the NFC protocol. Where the hub 102 wirelessly transmits the electrical power and data to the sensor node 104 based on the NFC protocol, or a similar power and communication scheme, the sensor node 104 further includes a coil 220. The coil 220 is connected to the transceiver 214 of the sensor node 104. Based on the properties of NFC, energizing the coil 218 causes a reciprocal energizing of the coil 220, which provides for the wireless transmission of both electrical power and data from the hub 102 to the sensor node 104.

Although not shown, the transceiver 206 of the hub 102 may, in some aspects, include one or more circuit components and/or general electronic components required for transmission of the electrical power and data from the hub 102, such as an amplifier, a modulator, and/or a modem, etc. Similarly, although not shown, the sensor node 104 may include one or more circuit components and/or general electronic components required for reception of the electrical power and data from the hub 102, as well as for transmission of the response data, such as an amplifier, a demodulator, and/or a modem, etc.

Figure 3A:
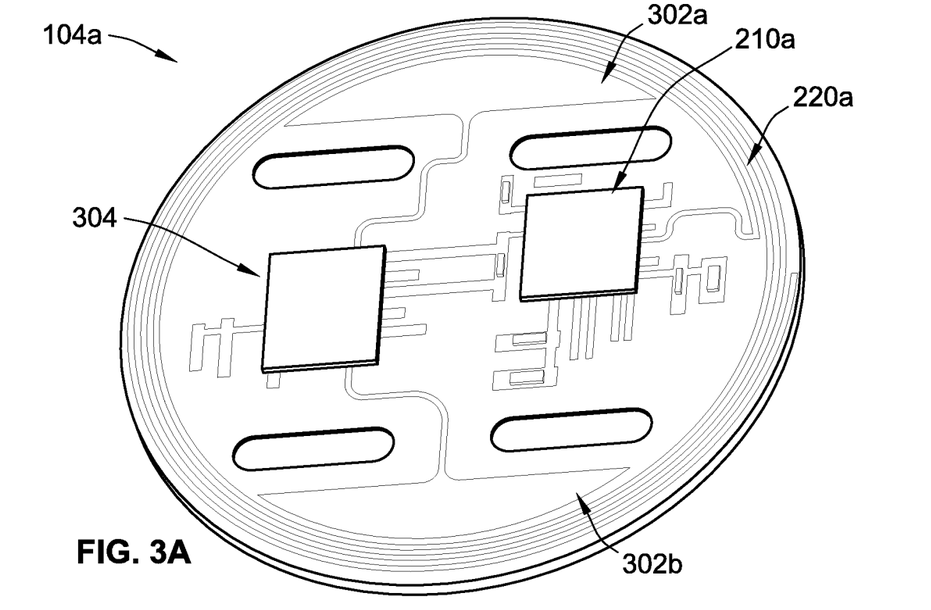
FIG. 3A shows a schematic diagram of an example sensor node used within the system of FIG. 1, in accord with aspects of the present disclosure.

Referring to FIGS. 3A-3D, FIGS. 3A-3D show perspective views of the hub 102 and the sensor node 104, both individually and coupled together, in accord with aspects of the present disclosure. More specifically, FIG. 3A shows a perspective view of a sensor node 104a. In the specific illustrated example, the sensor node 104a is designed for sensing electrical activity of the heart, such as an EKG or ECG sensor. The sensor node 104 includes a processor 210a. The processor 210a controls the processing of one or more algorithms and/or instructions for detecting the electrical activity of the heart. Additionally, the processor 210a executes one or more algorithms or instructions for controlling the communications (e.g., NFC communications) between the sensor node 104a and the hub 102.

FIG. 3A further shows the perspective view of the coil 220a. The coil 220a is a series of concentric loops of a continuous electrically conductive material (e.g., copper, silver, gold, aluminum, etc.) that extends around the perimeter of the sensor node 104a. The coil 220a is electrically connected to the processor 210a for providing (e.g., communicating or transferring) the electrical power and data to the processor 210a for extracting the data and powering the sensor node 104a.

The sensor node 104a further includes one or more components or sensors for sensing the ECG or EKG signals. As shown, the sensor node 104a can include two or more electrodes 302a and 302b. The electrodes 302a and 302b can be positioned on the top side of the sensor node 104a or on the bottom side of the sensor node 104a. The electrodes 302a and 302b detect the electrical signals generated by the heart beats as sensor information. The sensor node 104a further includes one or more components connected to the electrodes 302a and 302b, such as an MCU 304, for processing and/or analyzing the detected heart beat signals. Alternatively, the electrodes 302a and 302b can be connected to the processor 210a for processing and/or analyzing the detected heart beat signals.

Figure 3B:
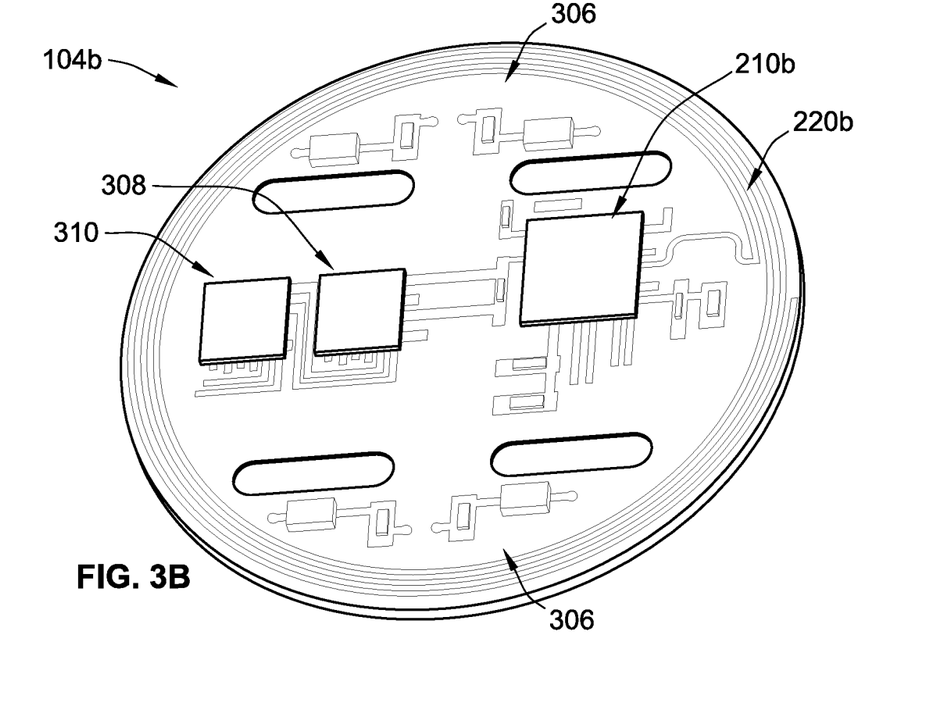
FIG. 3B shows a schematic diagram of another example sensor node used within the system of FIG. 1, in accord with aspects of the present disclosure.

Referring to FIG. 3B, FIG. 3B shows a perspective view of a sensor node 104b. In the specific illustrated example, the sensor node 104b is designed for sensing motion. The sensor node 104b includes a processor 210b. The processor 210b controls the processing of one or more algorithms and/or instructions for sensing motion. Additionally, the processor 210b executes one or more algorithms or instructions for controlling the communications (e.g., NFC communications) between the sensor node 104b and the hub 102.

FIG. 3B further shows the perspective view of the coil 220b. Like the coil 220a, the coil 220b is a series of concentric loops of a continuous electrically conductive material (e.g., copper, silver, gold, aluminum, etc.) that extends around the perimeter of the sensor node 104b. The coil 220b is electrically connected to the processor 210b for providing the electrical power and data to the processor 210b, and other components of the sensor node 104b, for extracting the data and powering the sensor node 104b.

The sensor node 104b further includes one or more components or sensors for sensing motion. In some aspects, the sensor node 104b can include one or more light sources 306, such as light emitting diodes, for indicating when the sensor node 104b is operating. Further, the sensor node 104b includes an accelerometer 308 and a gyroscope 310. The accelerometer 308 measures the force in up to three axes, and the gyroscope 310 measures the angular velocity with respect to the body axis. The accelerometer 308 and the gyroscope 310 are connected to the processor 210b for transmitting the sensor information to the processor 210b for subsequent processing and/or transmission to the hub 102.

Although FIGS. 3A and 3B illustrate an ECG or EKG sensor node 104a and a motion sensor node 104b, the system 100 can include other types of sensors. Non-limiting examples include heat flux sensors, accelerometers, gyroscopes, electrocardiogram (ECG or EKG) sensors, pressure sensors, heart rate monitors, galvanic skin response sensors, sweat sensors, and non-invasive blood pressure and blood oxygen saturation monitors, to name merely a few types of sensors.

Figure 3C:
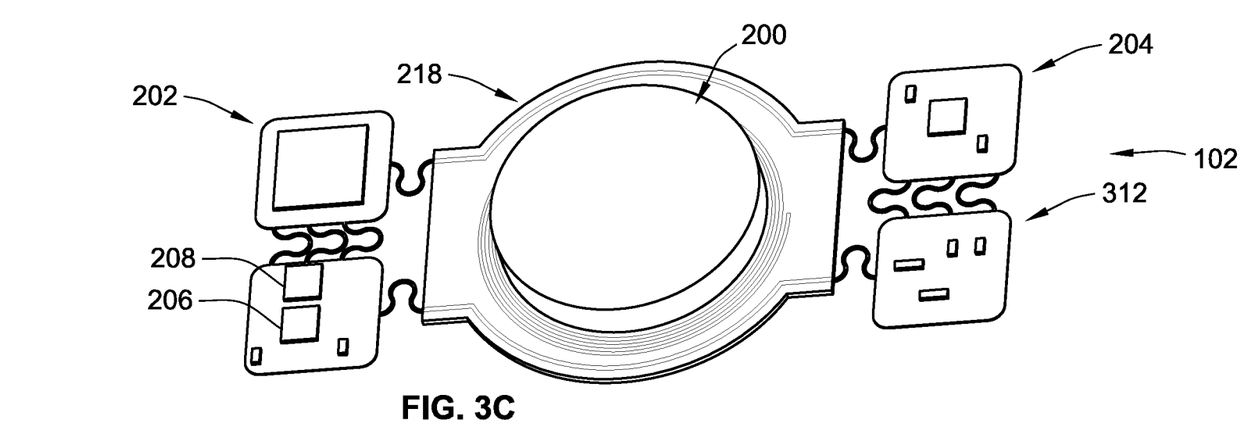
FIG. 3C shows a schematic diagram of a hub used within the system of FIG. 1, in accord with aspects of the present disclosure.

Referring to FIG. 3C, FIG. 3C shows a perspective view of the hub 102, in accord with aspects of the present disclosure. As described above, the hub 102 includes a power source 200. In the illustrated embodiment, the power source 200 is, for example, a lithium ion button battery. The hub 102 further includes the memory 202, the communications interface 204, and the processor 208. Also shown are the power transmitter and data transceiver 206 and the coil 218. Similar to the coils 220a and 220b, the coil 218 is a series of concentric loops of a continuous electrically conductive material (e.g., copper, silver, gold, aluminum, etc.).

In some aspects, the hub 102 can include one or more additional components. For example, the hub 102 can include circuitry 312 that allows for wireless charging of the power source 200. The coil 218 can be used for both wirelessly transmitting electrical power and data to the sensor node 104, as well as wirelessly receiving electrical power from, for example, an inductive wireless charger (not shown).

Figure 3D:
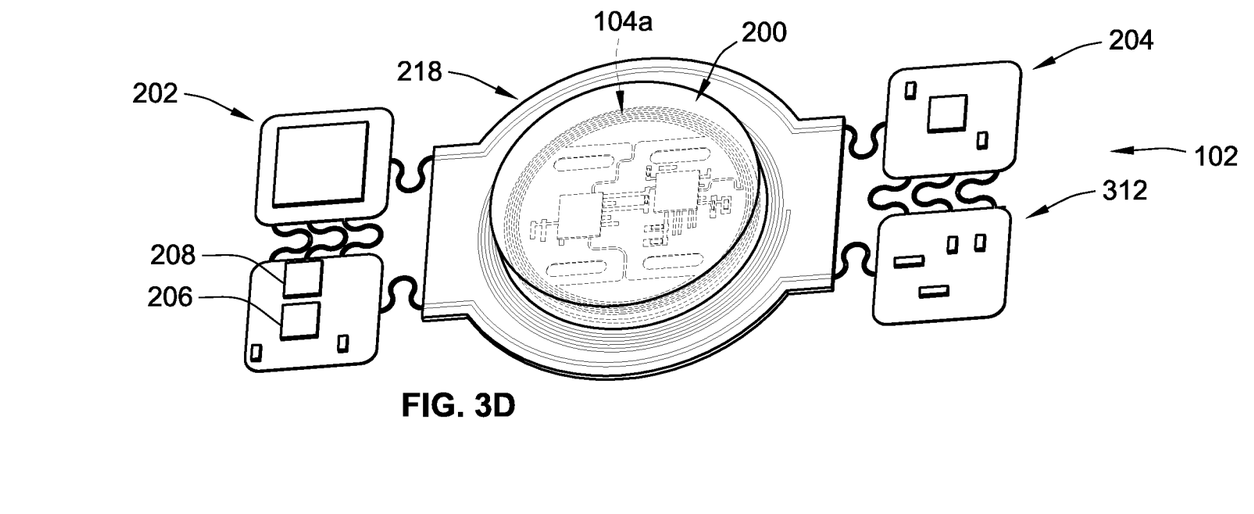
FIG. 3D shows a schematic diagram of a hub and a sensor node coupled together, in accord with aspects of the present disclosure.

Referring to FIG. 3D, the hub 102 and the sensor node 104a (but referring to all sensor nodes) are shown coupled together. The sensor node 104a is coupled to the back of the hub 102, opposite the power source 200, so that the sensor node 104a is in direct contact with the body 106 of the user. However, in some aspects, the sensor node 104a can be coupled to the other side of the hub 102, depending on the desired configuration and how the hub 102 is configured to attach to the user.

As described above, the hub 102 and the sensor node 104*a* are configured so that the coils 218 and 220*a* are co-located. Moreover, the hub 102 and the sensor node 104*a* are further configured so that the coils 218 and 220*a* are co-located and concentric. The co-located and concentric arrangement of the coils 218 and 220*a* maximizes the transmission of electrical power from the hub 102 to the sensor node 104*a*, and also maximizes the transmission of data between the hub 102 and the sensor node 104*a*. In the arrangement shown in FIG. 3D, the hub 102 can provide a continuous, periodic, semi-periodic, and on-demand supply of both electrical power and data to the sensor bode 104 for powering the sensor node 104. In response, the sensor node 104 generates and/or collects sensor information regarding the body 106 and transmits the sensor information back to the hub 102 as response data.

Figure 4:
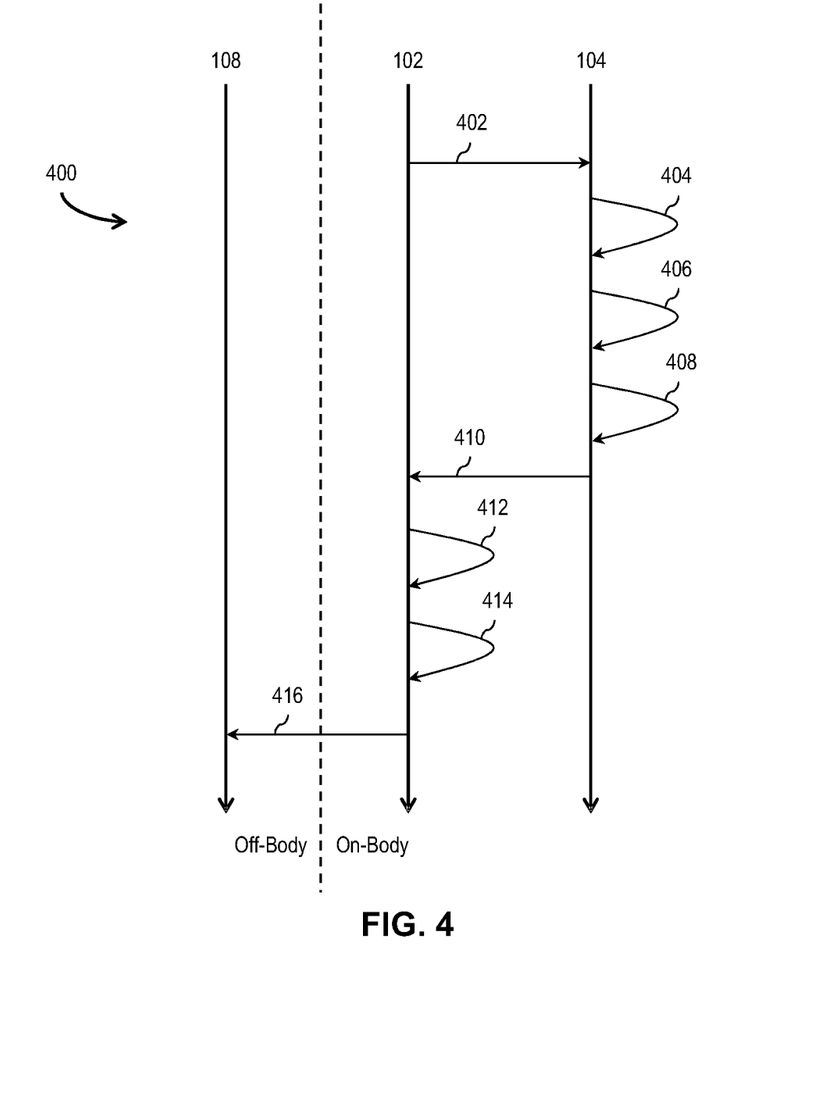
FIG. 4 shows a ladder diagram of electrical power and data transmission between a hub and a sensor node, in accord with aspects of the present disclosure.

Referring to FIG. 4, FIG. 4 shows a ladder diagram 400 illustrating communications between the hub 102, the sensor node 104, and the off-body computer device 108 within the system 100, in accord with aspects of the present disclosure. For the communications described with respect to the ladder diagram 400, the hub 102 and the sensor node 104 are coupled together in a co-located and concentric arrangement, such as that shown in FIG. 3D. Further, the coupled hub 102 and sensor node 104 are located on the body 106 of a user, such as that shown in FIG. 1. Further, the hub 102 is in wireless communication with the off-body computer device 108, such as a smartphone. However, the hub 102 may only be in communication with the off-body computer device 108 for the portions of the process in which the hub 102 communicates with the off-body computer device 108.

At step 402, the hub 102 transmits electrical power and data to the sensor node 104. According to an NFC communication scheme, the transmission of electrical power and data is via inductive coupling and transmission is of a signal at about 13.56 megahertz (MHz). The electrical power is transmitted as the carrier wave. The data is transmitted as the modulated signal within the carrier wave.

In some embodiments, the electrical power and data transmitted by the hub 102 is standard for all sensor nodes 104. Thus, sensor nodes 104 of varying sensing modalities are all designed to operate in response to the same electrical power and data transmitted by the hub 102. Alternatively, the electrical power and data transmitted by the hub 102 can vary depending on the type of sensor node 104 that is coupled to the hub 102. In which case, prior to step 402, a handshake can occur between the hub 102 and the sensor node 104. The handshake informs the hub 102 of the specific type of sensor node 104 or the specific sensing modalities supported by the sensor node 104 that is coupled to the hub 102. Based on the specific sensor node 104 or the sensing modalities of the sensor node 104, the hub 102 can vary the data, the electrical power, or both that are transmitted to the sensor node 104. For example, different algorithms and/or instructions can be sent to the sensor node 104, as part of the data transmitted to the sensor node 104 with the electrical power, depending on the specific functionality and/or modality of the sensor node 104. As a further example, different algorithms and/or instructions can be sent to the sensor node 104 depending on whether the sensor node 104 is a dumb node, a smart node, or somewhere between. Moreover, different algorithms and/or instructions can be sent to the sensor node 104 depending on whether the sensor information is to be transmitted back to the hub 102 as, for example, raw data or as data analyzed and/or processed by the processor 210 of the sensor node 104.

In some embodiments, sensor nodes 104 can receive some or all algorithms and/or instructions for operation from the hub 102. In alternative embodiments, sensor nodes 104 receive triggering information from the hub 102, but otherwise include algorithms and/or instructions for operation on-board, such as in the processor 210 or stored in separate memory (not shown).

At step 404, the sensor node 104 receives the transmitted electrical power and data from the hub 102. The sensor node 104 processes the received electrical power and data by, for example, rectifying the electrical power and demodulating the data.

By receiving the electrical power, the sensor node 104 activates to perform one or more processes related to collecting and/or generating sensor information. Specifically, at step 406, the sensor node 104 records data or sensor information generated and/or collected from one or more sensors 212 on the sensor node 104 based on the received electrical power. Further, at step 408, the sensor node 104 executes one or more sensor-specific algorithms based on the received electrical power to process and/or analyze the data or sensor information received from the one or more sensors 212. For example, at step 408, the sensor node 104 executes one or more processes for smoothing the sensor information, analyzing the sensor information, compressing the sensor information, filtering the sensor information, and the like. In some aspects, the processing includes executing one or more stored or transmitted (e.g., from the hub 102) pattern recognition algorithms to detect one or more pre-defined patterns in the data. Further, other processing of the data not explicitly listed herein can occur at step 408 (e.g., averaging, correlating, etc. of the sensor information). However, in some instances, step 408 can be omitted, such as in the case of a dumb node where the data or sensor information (e.g., raw data) from step 406 is streamed back to the hub 102 without being processed. Instead, for example, the processing and/or analyzing of the data or sensor information can instead be solely performed at the hub 102.

At step 410, the sensor node 104 transmits the processed and/or analyzed data or sensor information, or simply the collected and/or generated data or sensor information (e.g., raw data), to the hub 102 with the remaining received electrical power. The data is transmitted back to the hub 102 according to the NFC communication scheme via inductive coupling and transmission of a signal at about 13.56 megahertz (MHz). Because the electrical power is not being transmitted back to the hub 102, the data is transmitted as the sole signal, rather than as a modulated signal on an electrical power signal.

After receiving the response data from the sensor node 104, the hub 102 can perform one or more functions on the data. For example, at step 412, the hub 102 aggregates the processed and/or analyzed data or sensor information from the sensor node 104. Additionally, at step 414, the hub 102 further processes and/or analyzes the received data or sensor information from the sensor node 104. Similar to above, the processing can include, for example, smoothing the sensor information, analyzing the sensor information, compressing the sensor information, filtering the sensor information, and the like. The processing also can include executing one or more pattern recognition algorithms to detect one or more pre-defined patterns in the data. Based on, for example, the larger form factor of the hub 102, a more advanced processor 208 (as compared to processor 210), and/or the on-board power source 200, the processing at the hub 102 can be more advanced or provide optional processing. Further, other processing of the data not explicitly listed herein can occur at step 414 (e.g., averaging, correlating, etc. of the sensor information). However, one or both of steps 412 and 414 can be omitted or the order reversed depending on the specific desired functions of the hub 102.

At step 416, the hub 102 transmits the data or sensor information to the off-body computer device 108. The hub 102 transmits the data or sensor information based on one or more wireless communication protocols, such as, for example, Bluetooth, WiFi, Zigbee, etc. The off-body computer device 108 then performs one or more additional processes and/or functions on the data, depending on the specific desired functions of the off-body computer device 108.

The process described with respect to the ladder diagram 400 of FIG. 4 can be repeated continuously, periodically, semi-periodically, or on-demand for acquiring the sensor information over a period of time. Further, in some aspects, steps of the ladder diagram can be omitted when the process is repeated. For example, the hub 102 can initially send both electrical power and data to the sensor node 104, which causes the sensor node 104 to operate according to a predefined mode of operation. However, subsequent transmissions from the hub 102 can include only electrical power, such as to keep the sensor node 104 electrically powered, but do not include data. Alternatively, subsequent transmissions from the hub 102 can include only data, such as where the sensor node 104 includes an electrical power element (e.g., capacitor), but requires further data for operation. Thus, each repetition of the process described in the ladder diagram may vary depending on the variable configuration and functionality of the hub 102, the sensor node 104, or both.

As described above, the system 100 enjoys several benefits over existing systems. For example, the sensor node 104 operates independent of an on-board discrete power source. Accordingly, the sensor node 104 is not limited by the constraints on the form factor typically experienced by needing an on-board power source. Further, the sensor node 104 can operate continuously, periodically, semi-periodically, or on-demand without requiring an off-body computer device (e.g., reader), such as a smartphone, being in constant proximity to the sensor node. Additionally, de-coupling the backend electrical power and communications system from the frontend sensing system allows for different development schedules for each of the backend and the frontend, without requiring replacement of the entire system. The de-coupling of systems allows for faster development in system designs and architectures. Furthermore, the system 100 covers the spectrum of wearable sensing technology for users who are concerned with both episodic and continuous monitoring as the sensor node 104 can be used alone, such as being interrogated by the off-body computer device 108, or when coupled to the hub 102 for persistent monitoring. In accordance with some embodiments, the one or more hubs 102 can be supplied with 2 or more sensor nodes 104 in the form of a kit wherein the sensing nodes provide sensing modalities that are directed to a predefined class of injury, ailment or disease. For example, sensor nodes that detect temperature (e.g., thermal sensors) and physical motion (e.g., accelerometers and gyroscopes) can be included in a kit for multiple sclerosis or Parkinson's disease sensing and monitoring. And, for example, sensor nodes that detect heart rates (e.g., EKG, EMG, ECG and other biopotentials) as well as physical motion (e.g., accelerometers and gyroscopes) can be included in a kit for heart disease and stroke sensing and monitoring.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

What is claimed is:

1. An interchangeable sensor system comprising: a hub configured to be attached to a body of a user and to be selectively coupled to one or more sensor nodes, the hub being further configured to transmit electrical power and operational data wirelessly to the one or more sensor nodes; and at least one sensor node configured to be attached to the body of the user and configured to be selectively coupled to the hub and to receive the electrical power and the operational data wirelessly, the at least one sensor node including at least one sensor configured to generate sensor data responsive to the electrical power transmitted from the hub, the at least one sensor node being further configured to transmit the sensor data wirelessly to the hub for processing, aggregation, and/or transmission to an off-body computer device^ wherein the at least one sensor node is a plurality of sensor nodes, each sensor node of the plurality of sensor nodes including an application-specific sensor having a different sensing modality among the plurality of application-specific sensors, and the hub is configured to be selectively coupled to the sensor nodes of the plurality of sensor nodes one at a time.

2. The system of claim 1, wherein the hub includes a hub coil configured to transmit the electrical power and the operational data wirelessly, and the at least one sensor node includes a sensor node coil configured to receive the electrical power and the operational data and to transmit the sensor data.

3. The system of claim 2, wherein the hub and the at least one sensor are configured such that the hub coil and the sensor node coil are co-located when the at least one sensor node is coupled to the hub.

4. The system of claim 3, wherein the hub coil and sensor node coil are concentric when the at least one sensor node is coupled to the hub.

5. The system of claim 1, wherein the hub further includes a power source, and all electrical power required by the at least one sensor node for generating the sensor data is provided by the power source through the hub coil.

6. The system of claim 5, wherein the electrical power is transferred from the hub coil to the sensor node coil by induction.

7. The system of claim 6, wherein the hub further includes an inductive charging circuit configured to charge the power source based on an external power source by induction through the hub coil.

8. The system of claim 1, wherein the processor is configured to demodulate the electrical power to obtain the operational data.

9. The system of claim 1, wherein the hub includes memory configured to aggregate the sensor data from the at least one sensor node.

10. The system of claim 1, wherein the hub includes a processor, and the processor is configured to execute one or more application-specific algorithms based on the at least one sensor node currently coupled to the hub.

11. A method of acquiring sensor information, the method comprising: transmitting, by a hub, electrical power and operational data to at least one sensor node, the at least one sensor node being coupled to the hub, and the hub and the at least one sensor node being attached to a body of a user; receiving, by the at least one sensor node, the electrical power and the operational data transmitted by the hub; generating, by at least one sensor of the at least one senor node, sensor information associated with the body; transmitting, by the at least one sensor node, the sensor information to the hub; and aggregating, processing, and/or analyzing, by the hub, the sensor information received from the at least one sensor node, wherein the electrical power, the operational data, or a combination thereof are transmitted to the at least one sensor node continuously, periodically, or semi-periodically by the hub for acquiring the sensor information associated with the body, wherein only the electrical power is transmitted to the at least one sensor node continuously with the at least one sensor node coupled to the hub; recording, by the at least one sensor node, the sensor information in on-board memory prior to transmitting the sensor information to the hub; and executing, by the at least one sensor node, one or more location-specific algorithms based on the electrical power, the operational data, or a combination thereof to process and/or analyze the sensor information prior to transmitting the sensor information to the hub.

12. The method of claim 11, wherein the electrical power and the operational data are transmitted to the at least one sensor node continuously with the at least one sensor node coupled to the hub.

13. The method of claim 11, wherein only the operational data is transmitted to the at least one sensor node continuously with the at least one sensor node coupled to the hub.

14. The method of claim 11, wherein the hub includes a hub coil and the at least one sensor node includes a senor node coil.

15. The system of claim 14, wherein the hub and the at least one sensor node are configured such that the hub coil and the sensor node coil are co-located when the at least one sensor node is coupled to the hub.

16. The system of claim 15, wherein the hub coil and the sensor node coil are concentric when the at least one sensor node is coupled to the hub.

17. The method of claim 14, wherein the electrical power and the operational data are communicated to the at least one sensor node based on near field communication protocols.

18. The method of claim 11, further comprising:
modulating, by the hub, the electrical power with the operational data prior to transmitting the electrical power and the operational data; and
demodulating, by the at least one sensor node, the operational data from the electrical power to extract the operational data.

19. The method of claim 11, further comprising:
transmitting, by the hub, the sensor information to an off-body computer device after aggregating, processing, and/or analyzing the sensor information by the hub.

20. A method of acquiring sensor information, the method comprising:
modulating, by a hub, electrical power with operational data prior to transmitting the electrical power and the operational data;
transmitting, by the hub, the electrical power and the operational data to at least one sensor node, the at least one sensor node being coupled to the hub, and the hub and the at least one sensor node being attached to a body of a user;
receiving, by the at least one sensor node, the electrical power and the operational data transmitted by the hub;
demodulating, by the at least one sensor node, the operational data from the electrical power to extract the operational data;
generating, by at least one sensor of the at least one senor node, sensor information associated with the body;
transmitting, by the at least one sensor node, the sensor information to the hub; and
aggregating, processing, and/or analyzing, by the hub, the sensor information received from the at least one sensor node,
wherein the electrical power, the operational data, or a combination thereof are transmitted to the at least one sensor node continuously, periodically, or semi-periodically by the hub for acquiring the sensor information associated with the body.

21. The method of claim 20, further comprising:
transmitting, by the hub, the sensor information to an off-body computer device after aggregating, processing, and/or analyzing the sensor information by the hub.

* * * * *